(12) United States Patent
Sethuraman et al.

(10) Patent No.: US 8,425,948 B2
(45) Date of Patent: Apr. 23, 2013

(54) PROCESS FOR ISOLATION OF LUTEIN AND ZEAXANTHIN CRYSTALS FROM PLANT SOURCES

(75) Inventors: Swaminathan Sethuraman, Bangalore District (IN); Priya Madavalappil Kunhiraman, Bangalore District (IN)

(73) Assignee: Katra Phytochem India Private Limited, Bangalore District (IN)

( * ) Notice: Subject to any disclaimer, the term of this patent is extended or adjusted under 35 U.S.C. 154(b) by 0 days.

(21) Appl. No.: 13/144,016

(22) PCT Filed: Apr. 26, 2010

(86) PCT No.: PCT/IN2010/000263
§ 371 (c)(1),
(2), (4) Date: Jul. 11, 2011

(87) PCT Pub. No.: WO2010/125576
PCT Pub. Date: Nov. 4, 2010

(65) Prior Publication Data
US 2012/0108673 A1      May 3, 2012

(30) Foreign Application Priority Data
Apr. 27, 2009 (IN) ...................................... 964/2009

(51) Int. Cl.
*A01N 65/00* (2009.01)
(52) U.S. Cl.
USPC ........................................................ 424/725
(58) Field of Classification Search .................. None
See application file for complete search history.

(56) References Cited

U.S. PATENT DOCUMENTS
2007/0032683 A1   2/2007   Xu et al.

FOREIGN PATENT DOCUMENTS
| | | |
|---|---|---|
| SU | 1819619 A1 | 6/1993 |
| WO | 97/23436 A1 | 7/1997 |
| WO | 03/048284 A1 | 6/2003 |
| WO | 2006/114794 A1 | 11/2006 |
| WO | 2007/098520 A1 | 9/2007 |

OTHER PUBLICATIONS

International Search Report, mailed Jul. 3, 2011, for PCT/IN2010/000263, 4 Pages.
Ishida et al., "Carotenoid extraction from plants using a novel, environmentally friendly solvent," *J. Agric. Food Chem.* 57(3):1051-9, 2009, 9 Pages.
Bone et al., "Macular pigment response to a supplement containing meso-zeaxanthin, lutein and zeaxanthin," *Nutrition & Metabolism. Biomed Central* 4(12), May 11, 2007, 8 Pages.
Koloshina et al., "A method of extracting flavonoid cpds," Acc. No. 1994-331252, Thomson Scientific WPI, XP002623539, Corresponds to Soviet Union Patent Application No. 1819619, 1 Page, 1994.
Borges et al., "Preparation of black pepper oleoresin by alcohol extraction," *Die Nahrung—Food, VCH Verlagsgesellschaft* 37(2):127-30, 1993, 4 Pages.
Borges et al., "Preparation of nutmeg oleoresin by alcohol extraction," *Die Nahrung—Food, VCH Verlagsgesellschaft* 37(3):280-2, 1993, 3 Pages.

*Primary Examiner* — Michael Meller
(74) *Attorney, Agent, or Firm* — Seed IP Law Group PLLC

(57) ABSTRACT

The present invention provides for a process for isolation of carotenoids crystals comprising drying a plant part to obtain a meal and extracting the meal with alcohol at a temperature in the range of about 50° C. to 75° C. to obtain oleoresin. The oleoresin is enriched with alcohol at a temperature in the range of about 25° C. ° C. to 50° C. and hydrolyzed with alcoholic alkali at a temperature in the range of about 70° C. to 80° C. to obtain reaction mixture. The carotenoids crystals are precipitated from the reaction mixture by adding hot water followed by filtering, washing and drying the carotenoids crystals. The present invention also relates to carotenoids crystals comprising lutein and zeaxanthin in the ratios of about 10:1 or 5:1 or 1:1 obtained by a process which comprises mixing an oleoresin rich in lutein and an oleoresin rich in zeaxanthin separately in a ratios ranging from about 80:20 (w/w) to 90:10 (w/w) or about 70:30 (w/w) to 30:70 (w/w) or about 10:90 (w/w) to 20:80 (w/w) and homogenized to obtain a mixed oleoresin. The mixed oleoresin is then hydrolyzed with an alcoholic alkali at a temperature of about 70° C. to 80° C. to obtain a reaction mixture. The carotenoids crystals are precipitated by adding hot water to the reaction mixture to form a precipitate. Carotenoids crystals having lutein and zeaxanthin in a weight ratio of about 10:1 or 5:1 or 1:1 respectively are obtained by filtering, washing and drying the precipitate.

6 Claims, No Drawings

PROCESS FOR ISOLATION OF LUTEIN AND ZEAXANTHIN CRYSTALS FROM PLANT SOURCES

FIELD OF INVENTION

The present invention relates to a process for isolation of carotenoids crystals. The present invention particularly relates to a process for obtaining pure carotenoids crystals, wherein the carotenoids crystals thus obtained comprises xanthophylls such as lutein, zeaxanthin and low levels of β-carotene and cryptoxanthin.

The present invention also relates to a process for isolation of carotenoids crystals rich in lutein and zeaxanthin from different plants, to obtain carotenoids crystals of lutein and zeaxanthin in weight ratios of about 10:1, about 5:1 and about 1:1.

BACKGROUND OF THE INVENTION

Carotenoids are a class of natural fat-soluble pigments found principally in plants, algae, and photosynthetic bacteria, where they play a critical role in the photosynthetic process. They also occur in some non-photosynthetic bacteria, yeasts, and molds, where they carry out a protective function against damage by light and oxygen. Although animals appear to be incapable of synthesizing carotenoids, many animals incorporate carotenoids from their diet. Within animals, carotenoids provide bright coloration, serve as antioxidants, and can be a source for vitamin A activity (Ong and Tee 1992; Britton et al. 1995).

Carotenoids are defined by their chemical structure. The majority carotenoids are derived from a 40-carbon polyene chain, which could be considered the backbone of the molecule. This chain may be terminated by cyclic end-groups (rings) and may be complemented with oxygen-containing functional groups. The hydrocarbon carotenoids are known as carotenes, while oxygenated derivatives of these hydrocarbons are known as Xanthophylls. Beta-carotene, the principal carotenoid in carrots, is a familiar carotene, while Lutein, the major yellow pigment of marigold petals, is a common xanthophyll.

Xanthophylls have been proven scientifically to reduce the risk of age related macular degeneration (Moeller S M, Jacques P F, Blumberg J B "The potential role of dietary Xanthophylls in cataract and age related macular degeneration," Journal of the American College of Nutrition, 2000; 19: 522S-527S), control over LDL cholesterol (Chopra M., Thurnham D I, "Effect of Lutein on oxidation of low density lipoproteins (LDL) in vitro", Proceedings of the Nutrition Society, 1994; 53: 1993, #18A.), prevention of Coronary heart diseases (Howard A N, Williams N R, Palmer C R, Cambou J P, Evans A E, Foote J W, et al., "Do hydroxy-carotenoids prevent coronary heart disease") and free radicals scavenging and immunity enhancing (Chew B P, Wong M W, Wong T S, "Effects of Lutein from Marigold extract on immunity and growth of mammary tumors in mice," Anticancer Research, 1996; 16: 3689-3694).

Lutein (β-ε-carotene-3-3'-diol) and Zeaxanthin (β-β-carotene-3-3'-diol) belong to Xanthophylls group in the carotenoids family with highly reactive hydroxyl groups which cannot be synthesized by humans and animals.

U.S. Pat. No. 5,382,714 discloses process for isolation of pure lutein comprising from saponified marigold oleoresin containing free lutein.

U.S. Pat. No. 6,262,284 discloses process for extracting, saponifying, and isolating lutein and zeaxanthin, and a mixture of several rare carotenoids in high purity from plants.

U.S. Pat. No. 5,648,564 discloses a process for saponification of the marigold oleoresin with an aqueous alkali diluted with propylene glycol, resulting in the formation of lutein crystals.

U.S. Pat. No. 6,380,442 discloses a process of obtaining carotenoids from marigold oleoresin through hydrolysis by using iso-propyl alcohol with saponification. Further, the process involves cooling the reaction mixture to room temperature.

U.S. Pat. No. 6,504,067 discloses a process to obtain xanthophyll concentrates by refining the marigold oleoresin with sodium carbonate followed by neutralization, wherein the refined oleoresin was saponified using aqueous alkali.

WO 2006/114794 describes a procedure to isolate carotenoids, predominantly lutein from marigold flower petals.

U.S. Pat. No. 5,876,782 discloses in situ process for converting non-free form xanthophylls to free xanthophylls by transesterification of acyl-xanthophylls present in the biological material of the plant.

U.S. Pat. No. 6,743,953 describes a process of extraction of xanthophylls from dried marigold petals using hexane as solvent, involving saponification up to 3 hrs, subjecting the product to heating at 70° C. for a long time which may result in degenerated oxidative products in the saponified mass.

JP 113222708 A describes a process for isolating lutein from marigold oleoresin by saponification.

U.S. Pat. No. 6,784,351 discloses a marigold plant whose flower petals, leaves contain one or more of an enhanced zeaxanthin ratio, an enhanced neoxanthin plus violaxanthin ratio, an enhanced β-carotene ratio, an enhanced α-cryptoxanthin ratio, an enhanced phytoene ratio or an enhanced phytofluene ratio relative to that ratio in a non-mutant marigold. Also disclosed are methods of preparing such plants, oleoresins and comestible materials that have such carotenoid ratios.

However, there is a need for a process for isolation of carotenoids crystals wherein the dried plant meal is directly contacted with alcohol and wherein the carotenoids crystals thus obtained comprises xanthophylls such as lutein, zeaxanthin and low levels of β-carotene and cryptoxanthin.

These and other features, aspects, and advantages of the present subject matter will become better understood with reference to the following description and appended claims.

SUMMARY

The present invention provides a process for isolation of carotenoids crystals comprising drying a plant part to obtain a meal and extracting the meal with alcohol at a temperature in the range of about 50° C. to 75° C. to obtain oleoresin. The oleoresin is enriched with alcohol at a temperature in the range of about 25° C. to 50° C. and hydrolyzed with alcoholic alkali at a temperature in the range of about 70° C. to 80° C. to obtain reaction mixture. The carotenoids crystals are precipitated from the reaction mixture by adding hot water followed by filtering, washing and drying the carotenoids crystals.

An aspect of the present invention provides a process for producing an enriched oleoresin, said process comprising drying a plant part to obtain a meal; extracting said meal using alcohol at a temperature in the range of about 50° C. to 75° C. to obtain oleoresin; and enriching said oleoresin with alcohol at a temperature in the range of about 25° C. to 50° C. for about 10 to 20 minutes to obtain an enriched oleoresin.

Another aspect of the present invention provides carotenoids crystals comprising lutein and zeaxanthin in the weight ratios of about 10:1 obtained by a process which comprises contacting a plant part rich in lutein with alcohol and extracting at a temperature in the range of about 50° C. to 75° C. to obtain an extract, enriching the extract with alcohol at a temperature in the range of about 25° C. to 50° C. to obtain an enriched oleoresin rich in lutein. A plant rich in zeaxanthin is extracted by contacting a plant part rich in zeaxanthin with alcohol and extracting at a temperature in the range of about 50° C. to 75° C. to obtain another extract and enriching the extract with alcohol at a temperature in the range of about 25° C. to 50° C. to obtain an enriched oleoresin rich in zeaxanthin. The oleoresin rich in lutein is mixed with the oleoresin rich in zeaxanthin in weight ratios ranging from about 80:20 (w/w) to 90:10 (w/w). The mixed oleoresin is then hydrolyzed with an alcoholic alkali at a temperature in the range of about 70° C. to 80° C. to obtain a reaction mixture. Carotenoids crystals having lutein and zeaxanthin in a weight ratio of about 10:1 are precipitated from the reaction mixture by adding hot water. The carotenoids crystals are filtered, washed and dried.

Another aspect of the present invention provides carotenoids crystals comprising lutein and zeaxanthin in the weight ratio of about 5:1 obtained by a process which comprises of contacting a plant part rich in lutein with alcohol and extracting at a temperature in the range of about 50° C. to 75° C. to obtain an extract and further enriching the extract with alcohol at a temperature in the range of about 25° C. to 50° C. to obtain enriched oleoresin rich in lutein. A plant rich in zeaxanthin is extracted by contacting a plant part rich in zeaxanthin with alcohol and extracting at a temperature in the range of about 50° C. to 75° C. to obtain another extract and enriching the extract with alcohol at a temperature in the range of about 25° C. to 50° C. to obtain enriched oleoresin rich in zeaxanthin. The oleoresin rich in lutein is mixed with the oleoresin rich in zeaxanthin in weight ratios ranging from about 70:30 (w/w) to 30:70 (w/w). The mixed oleoresin is then hydrolyzed with an alcoholic alkali at a temperature in the range of about 70° C. to 80° C. to obtain a reaction mixture. Carotenoids crystals having lutein and zeaxanthin in a weight ratio of about 5:1 are precipitated from the reaction mixture by adding hot water. The carotenoids crystals are filtered, washed and dried.

Another aspect of the present invention provides carotenoids crystals comprising lutein and zeaxanthin in the weight ratios of about 1:1 obtained by a process which comprises of contacting a plant part rich in lutein with alcohol and extracting at a temperature in the range of about 50° C. to 75° C. to obtain an extract and further enriching the extract with alcohol at a temperature in the range of about 25° C. to 50° C. to obtain enriched oleoresin rich in lutein. A plant rich in zeaxanthin is extracted by contacting a plant part rich in zeaxanthin with alcohol and extracting at a temperature in the range of about 50° C. to 75° C. to obtain another extract and enriching the oleoresin rich in zeaxanthin with alcohol at a temperature in the range of about 25° C. to 50° C. to obtain enriched oleoresin rich in zeaxanthin. The oleoresin rich in lutein is mixed with the oleoresin rich in zeaxanthin in weight ratios ranging from about 10:90 (w/w) to 20:80 (w/w). The mixed oleoresin is then hydrolyzed with an alcoholic alkali at a temperature in the range of about 70° C. to 80° C. to obtain a reaction mixture. Carotenoids crystals having lutein and zeaxanthin in a weight ratio of about 1:1 are precipitated from the reaction mixture by adding hot water. The carotenoids crystals are filtered, washed and dried.

The present invention also provides carotenoids crystals comprising lutein and zeaxanthin, wherein a weight ratio of the lutein to zeaxanthin is about 10:1 or 5:1 or 1:1. Carotenoids crystals with these weight ratios made by the process as described above are also part of this invention. These weight ratios of lutein to zeaxanthin, specifically 10:1, 5:1 or 1:1, are critical in making the carotenoids more bioactive and bioavailable. The carotenoids crystals comprising lutein and zeaxanthin, wherein a weight ratio of the lutein to zeaxanthin is about 10:1, 5:1 or 1:1 are useful as antioxidants. These carotenoids crystals are particularly good for eye care.

The present invention has advantage in its time-temperature combination, organic friendly nature and usage of only safe class 3 solvents. All these factors contribute towards the yield and stability of the product and bring down the cost of production on a commercial scale. It also increases the safety of the product for use as a nutraceutical, cosmeceutical, food or dietary supplement.

This summary is provided to introduce a selection of concepts in a simplified form. This summary is not intended to identify key features or essential features of the claimed subject matter, nor is it intended to be used to limit the scope of the claimed subject matter.

DETAILED DESCRIPTION

The present invention provides a process for isolation of carotenoids crystals said process comprising drying a plant part to obtain a meal; extracting the meal with an alcohol at a temperature in the range of about 50° C. to 75° C. to obtain oleoresin; enriching the oleoresin with alcohol at a temperature in the range of about 25° C. to 50° C. to obtain enriched oleoresin; hydrolyzing the enriched oleoresin with alcoholic alkali at a temperature in the range of about 70° C. to 80° C. to obtain reaction mixture; adding hot water to the reaction mixture to precipitate carotenoids crystals.

In another embodiment of the present invention, the process of the invention further comprises filtering, washing and drying the carotenoids crystals.

The plant source rich in lutein and the plant source rich in zeaxanthin may be independently selected from the group consisting of marigold flowers (*Tagetes erecta*), marigold petals, mutant marigold flowers, mutant marigold petals, fruits of paprika, and berries of Chinese wolfberries (*Lycium barbarum*). In a specific embodiment, the plant source rich in lutein is selected from the group consisting of marigold flowers and marigold petals, and the plant source rich in zeaxanthin is selected from the group consisting of mutant marigold flowers, mutant marigold petals, fruits of paprika, and berries of Chinese wolfberries.

In a preferred embodiment, the plant parts used in the process of the present invention are ensilaged under controlled anaerobic conditions before drying.

In another embodiment of the present the alcohol employed for extracting the meal is ethanol, isopropanol, or mixtures thereof, preferably ethanol.

In another embodiment of the present invention the ratio of oleoresin to the alcohol for enriching the oleoresin is in the range of about 1:0.5 to 1:4 (w/v), preferably 1:1 (w/v).

In another embodiment of the present invention the alcoholic alkali is either ethanolic sodium hydroxide or ethanolic potassium hydroxide.

In another embodiment the ratio of reaction mixture to hot water is in the range of about 1:1 to 1:1.5.

Conventional methods for preparing the carotenoids crystals having both lutein and zeaxanthin, such as crystal blending after purifying lutein crystals and zeaxanthin crystals individually, results in varied ratios of lutein and zeaxanthin. Further, with such methods the recoveries of zeaxanthin purified crystals obtained above is very low which is not economical on a commercial scale. Thus, there is also a need for a process for isolation of carotenoids crystals rich in lutein and zeaxanthin from different plants in combining the oleoresin, to obtain carotenoids crystals of lutein and zeaxanthin in weight ratios of about 10:1, about 5:1 and about 1:1.

In an embodiment of the present invention, it provides a process for isolation of carotenoids crystals having lutein and zeaxanthin in a weight ratio of about 10:1, said process comprising:

contacting a plant source rich in lutein with an alcohol and extracting at a temperature of about 50° C. to 75° C. to obtain an extract;

enriching the extract with an alcohol at a temperature in the range of about 25° C. to 50° C. for about 10 to 20 minutes to obtain the oleoresin rich in lutein;

contacting a plant source rich in zeaxanthin with an alcohol and extracting at a temperature of about 50° C. to 75° C. to obtain an extract;

enriching the extract with an alcohol at a temperature in the range of about 25° C. to 50° C. for about 10 to 20 minutes to obtain the oleoresin rich in zeaxanthin;

mixing the oleoresin rich in lutein and the oleoresin rich in zeaxanthin in a ratio ranging from about 80:20 (w/w) to 90:10 (w/w) and homogenizing to obtain a mixed oleoresin;

hydrolyzing the mixed oleoresin with an alcoholic alkali at a temperature of about 70° C. to 80° C. to obtain a reaction mixture;

precipitating carotenoids crystals by adding hot water to the reaction mixture to form a precipitate; and obtaining carotenoids crystals having lutein and zeaxanthin in a weight ratio of about 10:1.

Another embodiment of the present invention is a process for isolation of carotenoids crystals having lutein and zeaxanthin in a weight ratio of about 5:1, said process comprising:

contacting a plant source rich in lutein with an alcohol and extracting at a temperature of about 50° C. to 75° C. to obtain an extract;

enriching the extract with an alcohol at a temperature in the range of about 25° C. to 50° C. for about 10 to 20 minutes to obtain the oleoresin rich in lutein;

contacting a plant source rich in zeaxanthin with an alcohol and extracting at a temperature of about 50° C. to 75° C. to obtain an extract;

enriching the extract with an alcohol at a temperature in the range of about 25° C. to 50° C. for about 10 to 20 minutes to obtain the oleoresin rich in zeaxanthin;

mixing the oleoresin rich in lutein and the oleoresin rich in zeaxanthin in a weight ratio ranging from about 70:30 (w/w) to 30:70 (w/w) and homogenizing to obtain a mixed oleoresin;

hydrolyzing the mixed oleoresin with an alcoholic alkali at a temperature of about 70° C. to 80° C. to obtain a reaction mixture;

precipitating carotenoids crystals by adding hot water to the reaction mixture to form a precipitate; and obtaining carotenoids crystals having lutein and zeaxanthin in a weight ratio of about 5:1.

Yet another embodiment of the present invention is a process for isolation of carotenoids crystals having lutein and zeaxanthin in a weight ratio of about 1:1, said process comprising:

contacting a plant source rich in lutein with an alcohol and extracting at a temperature of about 50° C. to 75° C. to obtain an extract;

enriching the extract with an alcohol at a temperature in the range of about 25° C. to 50° C. for about 10 to 20 minutes to obtain the oleoresin rich in lutein;

contacting a plant source rich in zeaxanthin with an alcohol and extracting at a temperature of about 50° C. to 75° C. to obtain an extract;

enriching the extract with an alcohol at a temperature in the range of about 25° C. to 50° C. for about 10 to 20 minutes to obtain the oleoresin rich in zeaxanthin;

mixing the oleoresin rich in lutein and the oleoresin rich in zeaxanthin in a weight ratio ranging from about 10:90 (w/w) to 20:80 (w/w) and homogenizing to obtain a mixed oleoresin;

hydrolyzing the mixed oleoresin with an alcoholic alkali at a temperature of about 70° C. to 80° C. to obtain a reaction mixture;

precipitating carotenoids crystals by adding hot water to the reaction mixture to form a precipitate; and obtaining carotenoids crystals having lutein and zeaxanthin in a weight ratio of about 1:1.

In yet another embodiment of the present invention, the process for isolation of carotenoids crystals having lutein and zeaxanthin in a weight ratio of about 10:1, about 5:1, and 1:1, further comprises washing with hot water at a temperature in the range of about 55° C. to 80° C., preferably about 75° C. and drying the carotenoids crystals.

In yet another embodiment of the present invention, the ratio of oleoresin to alcohol used for enriching the oleoresins in the process for isolation of carotenoids crystals having lutein and zeaxanthin in a weight ratio of about 10:1, about 5:1, and 1:1, is in the range of about 1:0.5 to 1:4 (w/v).

In yet another embodiment of the present invention, the alcohol used in the process for isolation of carotenoids crystals having lutein and zeaxanthin is selected from the group consisting of ethanol, isopropyl alcohol or mixtures thereof In a specific embodiment, the plant source rich in lutein and the plant source rich in zeaxanthin may be independently selected from the group consisting of marigold flowers (*Tagetes erecta*), marigold petals, mutant marigold flowers, mutant marigold petals, fruits of paprika, and berries of Chinese wolfberries (*Lycium barbarum*).

In a particular embodiment, the plant source rich in lutein is selected from the group consisting of marigold flowers and marigold petals, and the plant source rich in zeaxanthin is selected from the group consisting of mutant marigold flowers, mutant marigold petals, fruits of paprika, and berries of Chinese wolfberries.

In yet another embodiment of the present invention, the alcoholic alkali used in the process for isolation of carotenoids crystals is selected from a group consisting of ethanolic sodium hydroxide and ethanolic potassium hydroxide.

In yet another embodiment of the present invention, the ratio of reaction mixture to hot water for precipitating carotenoids crystals by adding hot water to the reaction mixture to form a precipitate, is in the range of about 1:1 to 1:1.4.

Another embodiment of the present invention provides a process for producing an enriched oleoresin, said process comprising:

drying a plant part to obtain a meal;

extracting said meal using alcohol at a temperature in the range of about 50° C. to 75° C. to obtain oleoresin; and enriching said oleoresin with alcohol at a temperature in the range of about 25° C. to 50° C. for about 10 to 20 minutes to obtain an enriched oleoresin.

In yet another embodiment of the present invention, the alcohol extracting the dried meal in the above process is selected from the group consisting of ethanol, isopropyl alcohol or mixtures thereof, preferably ethanol.

In yet another embodiment of the present invention, the plant used for drying to obtain the meal is selected from the group consisting of natural Marigold, mutated Marigold, Paprika and Chinese wolfberries (*Lycium barbarum*).

In yet another embodiment of the present invention, the plant parts are ensilaged under controlled anaerobic conditions before drying in the process for producing the enriched oleoresin.

In yet another embodiment of the present invention, the oleoresin is enriched with alcohol with the ratio of oleoresin to alcohol in the range of about 1:0.5 to 1:4 (w/v), preferably 1:1 (w/v) to 1:2 (w/v), in the process for producing the enriched oleoresin.

Another embodiment of the present invention provides carotenoids crystals having lutein and zeaxanthin in a weight ratio of about 10:1, obtained by a process comprising:

contacting a plant source rich in lutein with alcohol and extracting at a temperature in the range of about 50° C. to 75° C. to obtain oleoresin rich in lutein;

enriching the oleoresin rich in lutein with alcohol at a temperature in the range of about 20° C. to 50° C. to obtain enriched oleoresin rich in lutein;

contacting a plant source rich in zeaxanthin with alcohol and extracting at a temperature in the range of about 50° C. to 75° C. to obtain oleoresin rich in zeaxanthin;

enriching the oleoresin rich in zeaxanthin with alcohol at a temperature in the range of about 25° C. to 50° C. to obtain enriched oleoresin rich in zeaxanthin;

mixing an oleoresin rich in lutein and an oleoresin rich in zeaxanthin in a ratio ranging from about 80:20 (w/w) to 90:10 (w/w) and homogenizing to obtain a mixed oleoresin;

hydrolyzing the mixed oleoresin with an alcoholic alkali at a temperature in the range of about 70° C. to 80° C. to obtain a reaction mixture;

adding hot water to the reaction mixture to precipitate carotenoids crystals; and obtaining carotenoids crystals having lutein and zeaxanthin in a weight ratio of about 10:1, wherein the ratio of reaction mixture to hot water is 1: 1 to 1:1.5

Further, another embodiment of the present invention provides carotenoids crystals having lutein and zeaxanthin in a weight ratio of about 5:1, obtained by a process comprising:

contacting a plant source rich in lutein with alcohol and extracting at a temperature in the range of about 50° C. to 75° C. to obtain oleoresin rich in lutein;

enriching the oleoresin rich in lutein with alcohol at a temperature in the range of about 25° C. to 50° C. to obtain enriched oleoresin rich in lutein;

contacting a plant source rich in zeaxanthin with alcohol and extracting at a temperature in the range of about 50° C. to 75° C. to obtain oleoresin rich in zeaxanthin;

enriching the oleoresin rich in zeaxanthin with alcohol at a temperature in the range of about 25° C. to 50° C. to obtain enriched oleoresin rich in zeaxanthin;

mixing an oleoresin rich in lutein and an oleoresin rich in zeaxanthin in a ratio ranging from about 70:30 (w/w) to 30:70 (w/w) and homogenizing to obtain a mixed oleoresin;

hydrolyzing the mixed oleoresin with an alcoholic alkali at a temperature in the range of about 70° C. to 80° C. to obtain a reaction mixture;

adding hot water to the reaction mixture to precipitate carotenoids crystals; and obtaining carotenoids crystals having lutein and zeaxanthin in a weight ratio of about 5:1, wherein the ratio of reaction mixture to hot water is 1: 1 to 1:1.5.

Still another embodiment of the present invention provides carotenoids crystals having lutein and zeaxanthin in a weight ratio of about 1:1, obtained by a process comprising:

contacting a plant source rich in lutein with alcohol and extracting at a temperature in the range of about 50° C. to 75° C. to obtain oleoresin rich in lutein;

enriching the oleoresin rich in lutein with alcohol at a temperature in the range of about 25° C. to 50° C. to obtain enriched oleoresin rich in lutein;

contacting a plant source rich in zeaxanthin with alcohol and extracting at a temperature in the range of about 50° C. to 75° C. to obtain oleoresin rich in zeaxanthin;

enriching the oleoresin rich in zeaxanthin with alcohol at a temperature in the range of about 25° C. to 50° C. to obtain enriched oleoresin rich in zeaxanthin;

mixing an oleoresin rich in lutein and an oleoresin rich in zeaxanthin in a weight ratio ranging from about 10:90 (w/w) to 20:80 (w/w) and homogenizing to obtain a mixed oleoresin;

hydrolyzing the mixed oleoresin with an alcoholic alkali at a temperature in the range of about 70° C. to 80° C. to obtain a reaction mixture;

adding hot water to the reaction mixture to precipitate carotenoids crystals; and obtaining carotenoids crystals having lutein and zeaxanthin in a weight ratio of about 1:1, wherein the ratio of reaction mixture to hot water is 1: 1 to 1:1.5.

Yet another embodiment of the present invention relates to the process for isolation of carotenoids crystals having lutein and zeaxanthin in a weight ratio of about 1:1, wherein the filtration of said precipitated carotenoids crystals is carried out using filter press, centrifuge or neutch filter.

Yet another embodiment of the present invention relates to a process for isolation of carotenoids crystals having lutein and zeaxanthin in a weight ratio of about 10:1 or about 5:1 or about 1:1, wherein the carotenoids crystals are dried using fluid bed dryer.

The process of the present invention involves ensilaging plant parts under controlled anaerobic conditions to prevent the formation of degenerated oxidative products like epoxides, fix and enrich the carotenoids present, dehydration involving steps like screw press, shredding and fluidized bed drying using eco friendly producer gas as heating medium for the drier without any hazardous stack emission to obtain dried meal. The dried meal is solvent extracted using isopropyl alcohol or ethanol and is stripped for solvent to the least possible extent without much degradation to obtain oleoresin. The oleoresin thus obtained is enriched by washing the oleoresin two times with process water for 10-15 minutes at about 45° C. and three times with ethanol for 10-15 minutes at room temperature to obtain an enriched organic oleoresin containing at least double the concentration of xanthophylls than the initial oleoresin. The enriched oleoresin is homogenized. Hydrolysis of homogenized oleoresin is carried out with alcoholic alkali and the esters are saponified at temperature of about 70° C. to 80° C. for less than 30 minutes. The hydrolyzed carotenoids are precipitated by adding water such that the ratio of alcohol and water in the mixture is maintained in the range of 1:1 to 1:3 and the precipitate thus obtained is washed with hot water to remove impurities. The washed crystals are filtered using filter press and dried using fluid bed drier to remove moisture and volatile organic impurities.

The present invention has advantage in its organic friendly nature, time-temperature combination, and usage of safe class 3 solvents only. All these factors contribute towards the yield and stability of the product and bring down the cost of production on a commercial scale. It also increases the safety of the product for use as a nutraceutical, cosmeceutical, food or dietary supplement.

The present invention provides an effective process to isolate and purify carotenoids crystals from plant parts, in particular marigold flower petals, rich in predominantly Lutein, Zeaxanthin, or Lutein and Zeaxanthin in various combination. The cultivar *Tagetes erecta* is cultivated under dedicated organic package of practices including seed production, harvested and brought to the dehydration unit within hours of harvest. The package of practices includes non-GMO seed development and organic cultivation suiting specific agro climatic conditions. The organically grown flowers are then immediately taken for silaging in silos after physical cleaning and sprayed with organic friendly anti oxidant and silage additive at appropriate concentration under closed anaerobic conditions. The silaging is monitored through pH and temperature of the silage and ensured for complete fermentation over a period of two to three weeks. The silaged flowers are then harvested from the silos and subjected to dehydration process in series of steps. The silaged flowers are subjected to industrial screw press in two stages and are squeezed for the oozing water, bringing the moisture content from 88% to 75%. The squeezed flowers are then subjected to shredding before it is dried in fluid bed drier. The shredded flowers are dried in a fluid bed drier using hot air, generated by heating air with producer-gas flame produced by using an eco-friendly gassifier with absolutely stack free emission. The tunnel type industrial fluid bed drier (FBD) comprises of drying chambers with different temperatures across the tunnel from inlet, being the maximum temperature (85° C. to 90° C.) to the outlet at temperature (45° C. to 50° C.).

The transit time inside the FBD from inlet to outlet is only 30 minutes maximum, wherein the moisture level in the product is brought down to around 10% from around 75%. The advantage in this drying process is that the product is not subjected to high heat for long duration, minimizing the formation of degenerative oxidative products that could form due to heat and air for prolonged periods. The dried Marigold meal is pulverised using an industrial hammer mill and down sized to particles less than 400 microns.

The marigold flower meal thus obtained is subjected to solvent extraction using iso-propyl alcohol or ethanol as solvent in a battery of extractors under counter current extraction and at temperature not exceeding 75° C. to achieve maximum extractability of active principles viz., xanthophylls and carotenoids along with the other resinoids and lipids. The lean miscella is then concentrated in Falling film evaporators and Wiped film evaporators to bring down the solvent concentration to around 5% from 90% to 95% approximately. The concentrated miscella is then subjected to vacuum distillation to bring down the solvent level from 5% to 1%. This crude marigold oleoresin with 1% solvent level in it is further concentrated by stripping the solvent under a stream of nitrogen and steam to reduce the solvent levels to less than 1000 ppm in the final Marigold oleoresin. The marigold oleoresin thus obtained is homogenized under stirring in a reactor with 1:3 to 1:5 volumes of process water for 10 to 15 minutes at 45° C. The mixture is allowed to separate out and the separated layer is then filtered. The oleoresin on the filter is transferred back to the reactor and the washing is repeated once more similarly. The oleoresin thus obtained is homogenized under stirring in the same reactor with 1:1 volume of ethanol containing around 6.0% moisture for 10-20 minutes to obtain a uniform mixture at room temperature. The homogenized mass is then allowed to settle and separated after stopping the stirring. The bottom layer of the solvent is then drained off to retain the washed oleoresin in the reactor itself. Another 1:1 volume of ethanol is added to the retained oleoresin in the reactor and the homogenization, settling, separation and draining of the solvent is repeated two more times to get the enriched oleoresin. The enriched marigold oleoresin thus obtained contains almost two times Xanthophylls than that of the initial oleoresin before enrichment.

The homogenized enriched marigold oleoresin is then hydrolyzed in the same reactor with the addition of 1.5 to 2 volumes of 25% alcoholic sodium hydroxide solution, of the quantity of the marigold oleoresin, at a temperature ranging between 70° C. and 80° C. for a time period of not more than 30 minutes wherein the alcohol used is Ethanol with moisture content less than 6%. The degree of saponification is ensured by either thin layer chromatography or high pressure liquid chromatography and the final cooking is done for 10 minutes at the same temperature after ensuring the completion of saponification more than 99%.

Hot water generated in a separate vessel at a temperature of 65° C. to 75° C. is added to the saponified mass in a ratio of about 1:4 volumes calculated to the oleoresin and homogenised well for 10 minutes to aid the crystallization of carotenoids crystals. The ratio of absolute alcohol, already present in the reaction mixture, and water is maintained in the range of about 1:1 to 1:3, wherein the ratio of ethanol to water at 1:2, promotes better crystallization of carotenoids crystals and as well dissolves the unwanted impurities like soaps, lipids, fats and other organic matters.

The diluted mass is then filtered through a filter press by pumping the mass into the filter press aided by positive pressure using either Nitrogen or air. The collected mass inside the filter press plate is washed with hot water at a temperature of 65° C. to 75° C. with sufficient quantity of hot water until the pH is brought down to neutral at around 7.0.

The wet mass collected from the filter press is taken in Fluid bed drier at a temperature between 50° C. and 55° C. for a period of 1 hr or until the moisture level in the product is less than 1% and any organic volatile impurity is below the detectable limit determined by gas chromatography.

The resulting carotenoids crystals contain a minimum of 80% total Carotenoids, most often greater than 90%, determined by UV visible spectrophotometer. The carotenoids crystals comprise 45-89% (w/w) all trans-Lutein, 3-45% (w/w) trans-Zeaxanthin, less than 1% (w/w) each of the other carotenoids like, Beta carotene, Cryptoxanthin, Violaxanthin etc., and without almost any traces of cis-Luteins and epoxides determined by normal phase High pressure liquid chromatography (HPLC). The wax content in the crystals is about 10% w/w, when measured by Gas chromatography which is well within the limit accepted by Joint FAO/WHO Expert Committee on Food Additives (JECFA) limit.

The chemical recovery of the active principles viz., carotenoids and xanthophylls in the end product is between 65% w/w and 95% w/w from the input oleoresin, depending upon the desired final product purity and the variable conditions thereof utilized based on the above process parameters by slight modifications of the process herein.

The finished product of carotenoids crystals obtained are formulated and stabilized in bulk, in the form of powder, beadlets, granules, oil dispersions and water dispersions with concentrations varying from 1% to 40% by adding suitable pharma grade excipients and emulsifiers depending upon the end usage in line with the nutraceutical, cosmeceutical, food and dietary supplement products applications.

For the process for isolation of carotenoids crystals rich in lutein and zeaxanthin from two different plants, one rich in lutein and another rich in zeaxanthin to obtain carotenoids crystals at varying weight ratios of lutein and zeaxanthin ranging from about 10:1, about 5:1 and about 1:1, the zeaxanthin rich oleoresin is obtained from solvent extraction of a mutant variety of marigold plant that is sourced from Ball Horticulture Inc covered by the U.S. Pat. No. 6,784,351. Other sources of zeaxanthin rich oleoresin is Paprika and *Lycium barbarum*.

Plant parts from two different plants are dried separately to obtain two meals, one rich in lutein and the other rich in zeaxanthin. The plants particularly suited to the above process include but are not limited to natural Marigold (*Tagetes erecta*), mutated marigold, Paprika and Chinese wolfberries (*Lycium barbarum*) The dried meals are solvent extracted using alcohol separately and are stripped of solvent to the least possible extent without much degradation to obtain lutein rich oleoresin from lutein rich meal at a temperature in the range of about 50° C. to 75° C. and zeaxanthin rich oleoresin from zeaxanthin rich meal at a temperature of about 50° C. to 75° C.

The solvent extraction of the dried meal using ethanol is carried out at the temperature in the range of about 70° C. to 75° C. and when extracted with isopropyl alcohol, the temperature is in the range of about 55° C. to 58° C.

The oleoresins obtained by alcoholic extraction are additionally enriched by washing the oleoresin with water and ethanol at a temperature in the range of about 25° C. to 50° C. for about 10 to 20 minutes to obtain enriched oleoresins separately, one rich in lutein and the other rich in zeaxanthin.

The oleoresins, one rich in lutein and the other rich in zeaxanthin are mixed at three different specific weight ratio ranges of (i) 80:20 to 90:10, (ii) 70:30 to 30:70 and (iii) 10:90 to 20:80. These ratios are based on the carotenoid composition of the oleoresins. The carotenoid content of the oleoresins in turn depend on the type of extraction solvent employed; for instance, when alcohol is used for extraction, the oleoresin obtained is further enriched and hence the carotenoid content is further increased. Further, the carotenoid content in the oleoresin also depends on the oleoresin meal. These specific ratios of oleoresin while mixing facilitate in obtaining carotenoids crystals with lutein and zeaxanthin weight ratio (i) about 10:1, (ii) about 5:1 and (iii) about 1:1. The oleoresin mixture of one rich in lutein and the other rich in zeaxanthin in weight ratio (i) 80:20 to 90:10, provides carotenoids crystal with lutein and zeaxanthin in the weight ration about 10:1. Similarly, the oleoresin mixture of (ii) 70:30 to 30:70 provides the carotenoids crystals in the weight ratio about 5:1; and when the oleoresins are mixed in the weight ratio (iii) 10:90 to 20:80, the final carotenoids crystal of lutein and zeaxanthin obtained is about 1:1. These weight ratios of lutein to zeaxanthin, specifically 10:1, 5:1 and 1:1, are critical in making the lutein more bioactive and bioavailable.

The oleoresins mixture is homogenized by continued stirring at 40° C. in a hot water bath. Saponification of homogenized oleoresins is carried out with alcoholic alkali at temperature of about 70° C. to 80° C. for less than 30 minutes.

The saponified carotenoids are treated with hot water to obtain carotenoids crystals wherein ratio of reaction mixture to the hot water is in the range of about 1:1 to 1:1.5 (v/v) which corresponds to a ratio 4:1 (v/w) of hot water to oleoresin. The carotenoids crystals thus obtained are filtered using filter press and dried using fluid bed drier to remove moisture and volatile organic impurities. The filtered carotenoids crystals are washed with hot water maintained at 75° C., wherein the ratio of hot water to oleoresin used is 8:1 (v/w). The washed carotenoids crystals are dried using fluid bed drier.

Yet another embodiment of the present invention relates to a process for isolation of carotenoids crystals having lutein and zeaxanthin in a ratio of about 10:1, wherein said carotenoids crystals comprises of about 75% to 85% (w/w) of trans lutein, about 6% to 10% (w/w) trans-zeaxanthin and not more than 5% (w/w) each of other carotenoids measured by HPLC.

Yet another embodiment of the present invention relates to a process for isolation of carotenoids crystals having lutein and zeaxanthin in a weight ratio of about 5:1, wherein said carotenoids crystals comprises of about 70% to 80% (w/w) of trans lutein, about 10% to 20% (w/w) trans-zeaxanthin and not more than 5% (w/w) each of other carotenoids measured by HPLC.

Yet another embodiment of the present invention relates to a process for isolation of carotenoids crystals having lutein and zeaxanthin in a ratio of about 1:1, wherein said carotenoids crystals comprises of about 40% to 50% (w/w) of trans lutein, about 40% to 50% (w/w) trans-zeaxanthin and not more than 5% (w/w) each of other carotenoids measured by HPLC.

Yet another embodiment of the present invention relates to a process for isolation of carotenoids crystals having lutein and zeaxanthin in a weight ratio of about 10:1, wherein said carotenoids crystals rich in lutein and zeaxanthin contain about 10% (w/w) of total waxes when measured using Gas chromatography.

Yet another embodiment of the present invention relates to, a process for isolation of carotenoids crystals having lutein and zeaxanthin in a ratio of about 5:1, wherein said carotenoids crystals rich in lutein and zeaxanthin contain about 10% (w/w) of total waxes when measured using Gas chromatography.

Yet another embodiment of the present invention relates to a process for isolation of carotenoids crystals having lutein and zeaxanthin in a ratio of about 1:1, wherein said carotenoids crystals rich in lutein and zeaxanthin contain about 10% (w/w) of total waxes when measured using Gas chromatography.

Still another embodiment of the present invention relates to a process for isolation of carotenoids crystals having lutein and zeaxanthin in a weight ratio of about 10:1, wherein said carotenoids crystals rich in lutein and zeaxanthin are formulated in the form of powder, beadlets, granules, oil dispersion or water dispersion.

Still another embodiment of the present invention relates to a process for isolation of carotenoids crystals having lutein and zeaxanthin in a ratio of about 5:1, wherein said carotenoids crystals rich in lutein and zeaxanthin are formulated in the form of powder, beadlets, granules, oil dispersion or water dispersion.

Still another embodiment of the present invention relates to a process for isolation of carotenoids crystals having lutein and zeaxanthin in a ratio of about 1:1, wherein said carotenoids crystals rich in lutein and zeaxanthin are formulated in the form of powder, beadlets, granules, oil dispersion or water dispersion.

Yet another embodiment of the present invention relates to a process for isolation of carotenoids crystals having lutein and zeaxanthin in a weight ratio of about 10:1 or about 5: 1 or about 1:1, wherein said carotenoids crystals rich in lutein and zeaxanthin are used in food, dietary supplements, nutraceutical or cosmeceutical applications.

Still another embodiment of the present invention relates to a process for isolation of carotenoids crystals having lutein and zeaxanthin in a weight ratio of about 10:1, wherein said carotenoids crystals rich in lutein and zeaxanthin, contain 65%-95% (w/w) of the total carotenoids present in said oleoresin.

Still another embodiment of the present invention relates to a process for isolation of carotenoids crystals having lutein and zeaxanthin in a weight ratio of about 5:1, wherein said carotenoids crystals rich in lutein and zeaxanthin, contain 65%-95% (w/w) of the total carotenoids present in said oleoresin.

Still another embodiment of the present invention relates to a process for isolation of carotenoids crystals having lutein and zeaxanthin in a weight ratio of about 1:1, wherein said carotenoids crystals rich in lutein and zeaxanthin, contain 65%-95% (w/w) of the total carotenoids present in said oleoresin.

Yet another embodiment of the present invention relates to a process for isolating carotenoids crystals rich in lutein and zeaxanthin having lutein and zeaxanthin in a weight ratio of about 10:1, wherein the carotenoids crystals rich in lutein and zeaxanthin obtained after drying contains moisture level less than 1% and almost free from residual solvent traces.

Yet another embodiment of the present invention relates to a process for isolating carotenoids crystals rich in lutein and zeaxanthin having lutein and zeaxanthin in a weight ratio of about 5:1, wherein the carotenoids crystals rich in lutein and zeaxanthin obtained after drying contains moisture level less than 1% and almost free from residual solvent traces.

Yet another embodiment of the present invention relates to a process for isolating carotenoids crystals rich in lutein and zeaxanthin having lutein and zeaxanthin in a weight ratio of about 1:1, wherein the carotenoids crystals rich in lutein and zeaxanthin obtained after drying contains moisture level less than 1% and almost free from residual solvent traces.

Another embodiment of the present invention provides use of carotenoids crystals comprising a weight ratio of the lutein to zeaxanthin in about 10:1 or about 5:1 or about 1:1. as antioxidants.

Although the subject matter has been described in considerable detail with reference to certain preferred embodiments thereof, other embodiments are possible. As such, the spirit and scope of the appended claims should not be limited to the description of the preferred embodiment contained therein.

The invention will now be illustrated with working examples, which are intended to illustrate the working of invention and not intended to take restrictively to imply any limitations on the scope of the present invention.

EXAMPLE 1

Extraction of Oleoresin Using Iso-Propyl Alcohol as Solvent

Marigold meal (6.0 kg) having 8.99 gm/Kg (0.89%) of xanthophylls (with a carotenoids profile of 74.58% trans-lutein, 4.28% trans-zeaxanthin and 18.08% cis-isomers & epoxides) was taken in a 50 L capacity extractor with circulation facility. Iso-propyl alcohol (36L) having moisture content less than 1.0% was added to the extractor and circulated. The temperature was raised to 55° C. and maintained for 1 hr under circulation. After 1 hr the extract was drained and collected in a miscella tank. The extraction was repeated for two times with the same volume of iso-propyl alcohol (36 L) under the same conditions of temperature and time. The extracts obtained were collected in the miscella tank. The fourth and fifth extractions were carried out using 30L of iso-propyl alcohol in each extraction under circulation and at a temperature of 58° C. 152 L of miscella collected from the five extractions was taken to an evaporator, preferably a falling film evaporator or a wiped film evaporator to obtain a concentrated miscella containing 70% solids and 30% solvent. The concentrated miscella was distilled further in a distillation unit under atmospheric pressure to increase the concentration of solids to 95% with a solvent level of around 5%. The solvent was distilled under reduced pressure (450 to 600 mm Hg) to reduce the solvent level to less than 1%. The total amount of solvent recovered was 136 L with a gas chromatographic purity of more than 99% and with a moisture level of 0.28%. 960 gms of oleoresin containing 49.68 g/kg of xanthophylls (4.97% xanthophylls) was obtained with a recovery of 88.42%. The oleoresin thus obtained exhibited a carotenoids profile containing 70.98% trans-lutein, 5.30% trans-zeaxanthin and 20.12% of cis-isomers/epoxides.

EXAMPLE 2

Hydrolysis of the Oleoresin with Alcoholic Alkali 100.26 g of the marigold oleoresin obtained from Example 1 containing 49.68 g/kg of xanthophylls (4.97% xanthophylls) was homogenised for 10 minutes in a 1000 ml round bottomed flask under continuous stirring at a temperature of 40° C. in a hot water bath. Ethanolic NaOH was prepared by taking 49.60 gms of NaOH with purity of 95% and dissolving it in 200 ml of ethanol. The prepared ethanolic NaOH was slowly added into reaction vessel containing the homogenised marigold oleoresin (1:2 volumes of oleoresin). The saponification reaction was carried out at a temperature of 75° C. for 30 minutes. After ensuring the degree of saponification to be more than 99% by HPLC, 400 ml of demineralised hot water maintained at a temperature of 70° C. was added to the saponified marigold oleoresin and stirring was continued for 10 minutes. The diluted saponified marigold oleoresin comprising carotenoids crystals was filtered in a Buchner funnel to recover the carotenoids crystals. The carotenoids crystals thus obtained were washed with 1600 ml hot water to remove the impurities and bring down the pH of the effluent to neutral around 7.0. The wet crystals were then collected from the filter and dried in a vacuum drier at a temperature around 50° C. for 3 hours under reduced pressure.

Purified xanthophyll crystals (5.80 g) were obtained as sticky powder and the physical recovery of the final product was 5.78%. The carotenoids crystals obtained contained 58.50% carotenoids (determined by UV-Visible spectrophotometer) of which 84.10% was all trans-Lutein, 3.60% all trans-Zeaxanthin, 0.12% Beta Carotene, 0.31% Cryptoxanthin and with 6.80% of cis-luteins and epoxides (determined by HPLC). The carotenoids crystals thus obtained contained 16.20% w/w wax content when measured using gas-chromatography. The chemical recovery of the final product was 68.07% against the input Oleoresin. The final product contained a moisture content of 0.98% and contained 1400 ppm of Iso-propyl alcohol by gas chromatography analysis.

EXAMPLE 3

Extraction of Oleoresin Using Iso-Propyl Alcohol as Solvent and Washing with Ethanol to Enrich the Oleoresin Marigold meal (6.1 kg) having 8.99 gm/Kg (0.89%) of xanthophylls (with a carotenoids profile of 74.58% trans-lutein, 4.28% trans-zeaxanthin and 18.08% cis-isomers & epoxides) was taken in a 50 L capacity extractor with circulation facility. Iso-propyl alcohol (36 L) having moisture content less than 1.0% was added to the extractor and circulated. The temperature was raised to 55° C. and maintained for 1 hr under circulation. After 1 hr the extract was drained and collected in a miscella tank. The extraction was repeated for two times with the same volume of iso-propyl alcohol (36 L) under the same conditions of temperature and time. The extracts obtained were collected in the miscella tank. The fourth and fifth extractions were carried out using 30L of iso-propyl alcohol in each extraction under circulation and at a temperature of 58° C. 150 L of miscella collected from the five extractions was taken to an evaporator, preferably a falling film evaporator or a wiped film evaporator to obtain a concentrated miscella containing 70% solids and 30% solvent. The concentrated miscella was distilled further in a distillation unit under atmospheric pressure to increase the concentration of solids to 95% with a solvent level of around 5%. The solvent was distilled under reduced pressure (450 to 600 mm Hg) to reduce the solvent level to less than 1%. The total amount of solvent recovered was 135 L with a gas chromatographic purity of more than 99% and with a moisture level of 3%. 982 gms of oleoresin containing 50.72 g/kg of xanthophylls (5.07% xanthophylls) was obtained with a recovery of 90.82%. The oleoresin thus obtained exhibited a carotenoids profile containing 70.22% trans-lutein, 5.43% trans-zeaxanthin and 20.82% of cis-isomers/epoxides.

The oleoresin (165.68 g) containing 50.72 g/kg of xanthophylls, obtained by extraction with iso-propyl alcohol, was homogenized at room temperature with 165 ml of ethanol containing 6% moisture in a conical flask for 10 minutes to obtain a homogeneous uniform mixture. The contents of the mixture were allowed to settle and separate. The bottom layer of the solvent was drained and the oleoresin thus obtained was retained in the conical flask. The process was repeated for two times by adding 165 ml of ethanol each time to enrich the oleoresin. 64.25 g of enriched oleoresin containing 119.86 g/kg of xanthophylls (11.98% xanthophylls) was obtained with a chemical recovery of 91.64%. The enriched oleoresin thus obtained exhibited a carotenoids profile containing 71.41% trans-lutein, 4.62% trans-zeaxanthin and 20.16% of cis-isomers/epoxides.

EXAMPLE 4

Hydrolysis of the Enriched Oleoresin with Alcoholic Alkali 44.826 g of the enriched marigold oleoresin obtained in example 3 containing 119.86 g/kg of xanthophylls (11.98% xanthophylls) was homogenised for 10 minutes in a 500 ml round bottomed flask under continuous stirring at a temperature of 40° C. in a hot water bath. Ethanolic NaOH was prepared by taking 22.40 gms of NaOH with purity of 95% and dissolving it in 90 ml of ethanol. The prepared ethanolic NaOH was slowly added into reaction vessel containing the homogenised marigold oleoresin (1:2 volumes of oleoresin). The saponification reaction was carried out at a temperature of 75° C. for 30 minutes. After ensuring the degree of saponification to be more than 99% by HPLC, 180 ml of demineralised hot water maintained at a temperature of 70° C. was added to the saponified marigold oleoresin and stirring was continued for 10 minutes. The diluted saponified marigold oleoresin comprising carotenoids crystals was filtered in a Buchner funnel to recover the carotenoids crystals. The carotenoids crystals thus obtained were washed with 720 ml hot water to remove the impurities and bring down the pH of the effluent to neutral around 7.0. The wet crystals were then collected from the filter and dried in a vacuum drier at a temperature around 50° C. for 3 hours under reduced pressure.

Purified xanthophyll crystals (4.0 g) were obtained and the physical recovery of the final product was 8.92%. The carotenoids crystals obtained contained 90.78% carotenoids (determined by UV-Visible spectrophotometer) of which 93.99% was all trans-Lutein, 4.90% all trans-Zeaxanthin, 0.23% Beta Carotene and 0.5% Cryptoxanthin and without any traces of cis-luteins and epoxides (determined by HPLC). The carotenoids crystals thus obtained contained 8.56% w/w wax content when measured using gas-chromatography. The chemical recovery of the final product was 67.58%. The final product contained a moisture content of 0.47% and could not be detected for any traces of residual solvents by gas chromatography analysis.

EXAMPLE 5

Extraction of Oleoresin Using Isopropyl Alcohol as Solvent and Washing with Ethanol to Enrich the Oleoresin Marigold meal (100 kg) having 9.44 gm/kg (0.94%) of xanthophylls (with a carotenoids profile of 73.98% trans-lutein, 4.52% trans-zeaxanthin and 18.28% cis-isomers & epoxides) was taken in a 1000 L capacity extractor with circulation facility. Iso-propyl alcohol (600 L) having moisture content less than 0.1% was added to the extractor and circulated. The temperature was raised to 55° C. and maintained for 1 hr under circulation. After 1 hr the extract was drained and collected in a miscella tank. The extraction was repeated two times with the same volume of iso-propyl alcohol (600 L) under the same conditions of temperature and time. The extracts obtained were collected in the miscella tank. The fourth and fifth extractions were carried out using 500 L of iso-propyl alcohol in each extraction under circulation and at a temperature of 58° C. The miscella collected from the five extractions (2500 L) was taken into an evaporator, preferably a falling film evaporator or a wiped film evaporator to obtain a concentrated miscella containing 70% solids and 30% solvent. The concentrated miscella was then distilled further in a distillation unit under atmospheric pressure to increase the concentration of solids to 95% with a solvent level of around 5%. The solvent was further distilled under reduced pressure (450 to 600 mm Hg) to reduce the solvent level to less than 1%. The total amount of solvent recovered was 2275 ltrs. with a gas chromatographic purity of more than 99% and with a moisture level of 3%.

Oleoresin (16.5 Kg) containing 52.32 g/kg of xanthophylls (5.23% Xanthophylls) was obtained with a chemical recovery of 91.44%. The oleoresin thus obtained exhibited a carotenoids profile containing 71.62% T-Lutein, 5.39% T-Zeaxanthin and 19.51% of Cis-isomers/Epoxides.

Oleoresin (16.5 kg) containing 52.32 g/kg of xanthophylls, obtained by extraction with iso-propyl alcohol, was homogenized at room temperature in a 100 L reactor with 16.5 L of ethanol containing 6% moisture for 10 minutes to obtain a homogeneous uniform mixture. The contents of the mixture were allowed to settle and separate. The bottom layer of the solvent was drained and the oleoresin thus obtained was retained in the reactor. The process was repeated for two times by adding 16.5 L of ethanol each time to enrich the oleoresin.

6.52 kg of enriched oleoresin containing 120.22 g/kg of xanthophylls (12.02% xanthophylls) was obtained with a chemical recovery of 90.80%. The enriched oleoresin thus obtained exhibited a carotenoids profile containing 71.98% trans-lutein, 4.39% trans-zeaxanthin and 19.78% of cis-isomers/epoxides.

EXAMPLE 6

Hydrolysis of the Enriched Oleoresin with Alcoholic Alkali 6.52 kg The enriched marigold oleoresin obtained in example 5 containing 120.22 g/kg of xanthophylls (12.02% xanthophylls) was homogenised for 10 minutes in a 100 L reactor under continuous stirring at a temperature of 40° C. with either steam or hot water in the jacket of the reactor as heating medium. Ethanolic NaOH was prepared by taking 3.26 Kgs of NaOH with purity of 95% and dissolving it in 13.0 L of ethanol. The prepared ethanolic NaOH was slowly added into the reactor containing the homogenised marigold oleoresin (1:2 volumes of oleoresin). The saponification reaction was carried out at a temperature of 75° C. for 30 minutes. After ensuring the degree of saponification to be more than 99% by HPLC, 26 L of demineralised hot water maintained at a temperature of 70° C. was added to the saponified marigold oleoresin and the stirring was continued for 10 minutes. The diluted saponified marigold oleoresin comprising carotenoids crystals was filtered in a filter press to recover the crystals. The carotenoids crystals thus obtained were washed with 104 L of additional hot water pumped through the filter press to remove the impurities and bring down the pH of the effluent to neutral around 7.0. The wet crystals were then collected from the filter press and dried in a fluid bed drier at a temperature around 55° C. for 1 hour.

Purified xanthophyll (706 g) crystals were obtained and the physical recovery of the final product was 10.82%. The carotenoids crystals obtained contained 91.12% carotenoids (determined by UV-Visible spectrophotometer) of which 93.67% was all trans-Lutein, 5.14% all trans-Zeaxanthin, 0.26% beta-carotene and 0.52% cryptoxanthin and without any traces of cis-luteins and epoxides (determined by HPLC). The carotenoids crystals thus obtained contained 8.12% w/w wax content when measured using gas-chromatography. The chemical recovery of the final product was 82.07%. The final product contained a moisture content of 0.42% and could not be detected for any traces of residual solvents by gas chromatography analysis.

EXAMPLE 7

Extraction of Oleoresin Using Ethanol as the Solvent and Washing with Ethanol to Enrich the Oleoresin Marigold meal (100 kg) having 9.44 gm/kg (0.94%) of xanthophylls (with a carotenoids profile of 73.98% trans-lutein, 4.52% trans-zeaxanthin and 18.28% cis-isomers & epoxides) was taken in 1000 L capacity extractor with circulation facility. Ethanol (600 L) having moisture content less than 3.0% was added to the extractor and circulated. The temperature was raised to 75° C. and maintained for 1 hr under circulation. After 1 hr the extract was drained and collected in a miscella tank. The extraction was repeated for two times with the same volume of ethanol (600 L) under the same condition of temperature and time. The extracts obtained were collected in the miscella tank. The fourth and fifth extractions were carried out using 500 L of ethanol in each extraction under circulation at the same temperature. The miscella collected from the five extractions (2540 L) was taken to an evaporator, preferably a falling film evaporator or a wiped film evaporator to obtain a concentrated miscella containing 70% solids and 30% solvent. The concentrated miscella was then distilled further in a distillation unit under atmospheric pressure to increase the concentration of solids to 95% with a solvent level of around 5%. The solvent was further distilled under reduced pressure (450 to 600 mm Hg) to reduce the solvent level to less than 1%. The total amount of solvent recovered was 2286 L with a gas chromatographic purity of more than 99% and with a moisture level of 4.2%.

Oleoresin (18.20 kg) containing 46.12 g/kg of xanthophylls (4.61% xanthophylls) was obtained with a chemical recovery of 88.96%. The oleoresin thus obtained exhibited a carotenoids profile containing 71.02% trans-lutein, 5.52% trans-zeaxanthin and 19.81% of cis-isomers/epoxides.

Oleoresin (18.20 kg) containing 46.12 g/kg of xanthophylls, obtained by extraction with Ethanol, was homogenized at 45° C. with 90 Liters of process water in the 200 L reactor for 20 minutes. The content of the mixture was allowed to settle and separate. The separated mixture was filtered under vacuum. The Marigold oleoresin thus obtained on the filter was transferred into the vessel. This process was repeated once more with the same 90 Liters of process water under the same temperature to remove all water soluble impurities. To the oleoresin obtained 18.0 L of ethanol containing 6% moisture was added and stirred at room temperature for 10 minutes to obtain a homogeneous uniform mixture. The contents of the mixture were allowed to settle and separate. The bottom layer of the solvent was drained and the oleoresin thus obtained was retained in the reactor. The process was repeated two times by adding another 18.0 L of ethanol each time to wash the oleoresin.

Enriched oleoresin (6.44 kg) containing 118.99 g/kg of xanthophylls (11.89% xanthophylls) was obtained with a chemical recovery of 91.32%. The enriched oleoresin thus obtained exhibited a carotenoids profile containing 70.95% trans-lutein, 4.52% trans-zeaxanthin and 19.66% of cis-isomers/epoxides.

EXAMPLE 8

Hydrolysis of the Enriched Oleoresin with Alcoholic Alkali 6.44 kg of the enriched marigold oleoresin obtained in Example 7 containing 118.99 g/kg of xanthophylls (11.89% xanthophylls) was homogenised for 10 minutes in a 100 L reactor under continuous stirring at a temperature of 40° C. with either steam or hot water in the jacket of the reactor as heating medium. Ethanolic NaOH was prepared by taking 3.22 kg of NaOH with purity of 95% and dissolving it in 13.0 L of ethanol. The prepared ethanolic NaOH was slowly added into reactor containing the homogenised mass (1:2 volumes of oleoresin). The saponification reaction was carried out at a temperature of 75° C. for 30 minutes. After ensuring the degree of saponification to be more than 99% by HPLC, 26 L of demineralised hot water maintained at a temperature of 70° C. was added to the reacted mass and the stirring was continued for 10 minutes. The diluted saponified marigold oleoresin comprising the carotenoids crystals was filtered in a filter press to recover the crystals. The carotenoids crystals thus obtained were washed with 105 L of additional hot water pumped through the filter press to remove the impurities and bring down the pH of the effluent to neutral around 7.0. The wet crystals were then collected from the filter press and dried in a fluid bed drier at a temperature around 55° C. for 1 hour.

Purified xanthophyll crystals (677 gms) were obtained and the physical recovery of the final product was 10.51%. The carotenoids crystals obtained contained 91.26% carotenoids (determined by UV-Visible spectrophotometer) of which 93.62% was all trans-lutein, 5.11% all trans-zeaxanthin, 0.26% beta carotene and 0.51% cryptoxanthin and without any traces of cis-luteins and epoxides (determined by HPLC). The carotenoids crystals thus obtained, contained 8.29% w/w wax content when measured using Gas-chromatography. The chemical recovery of the final product was 80.62%. The final product contained a moisture content of 0.45% and could not be detected for any traces of residual solvents by gas chromatography analysis.

EXAMPLE 9

Extraction of Oleoresin Using Ethanol as the Solvent for Extraction and Washing with Ethanol to Enrich the Oleoresin Marigold meal (100 kg) having 12.12 gm/kg (1.212%) of xanthophylls (with a carotenoids profile of 76.22% trans-lutein, 4.51% trans-zeaxanthin and 17.92% cis-isomers & epoxides) was taken in 1000 L capacity extractor with circulation facility. Ethanol (600 L) having moisture content less than 3.0% was added to the extractor and circulated. The temperature was raised to 75° C. and maintained for 1 hr under circulation. After 1 hr the extract was drained and collected in a miscella tank. The extraction was repeated for two times with the same volume of ethanol (600 L) under the same condition of temperature and time. The extracts obtained were collected in the miscella tank. The fourth and fifth extractions were carried out using 500 L of ethanol in each extraction under circulation at the same temperature. The miscella collected from the five extractions (2540 L) was taken to an evaporator, preferably a falling film evaporator or a wiped film evaporator to obtain a concentrated miscella containing 70% solids and 30% solvent. The concentrated miscella was then distilled further in a distillation unit under atmospheric pressure to increase the concentration of solids to 95% with a solvent level of around 5%. The solvent was further distilled under reduced pressure (450 to 600 mm Hg) to reduce the solvent level to less than 1%. The total amount of solvent recovered was 2280 L with a gas chromatographic purity of more than 99% and with a moisture level of 3.8%.

Oleoresin (19.28 kg) containing 58.38 g/kg of xanthophylls (5.838% xanthophylls) was obtained with a chemical recovery of 92.87%. The oleoresin thus obtained exhibited a carotenoids profile containing 74.22% trans-lutein, 5.58% trans-zeaxanthin and 19.02% of cis-isomers/epoxides.

Oleoresin (19.28 kg) containing 58.38 g/kg of xanthophylls, obtained by extraction with Ethanol, was homogenized at 45° C. with 96 Liters of process water in the 200 L reactor for 20 minutes. The content of the mixture was allowed to settle and separate. The separated mixture was filtered under vacuum. The Marigold oleoresin thus obtained on the filter was transferred into the vessel. This process was repeated once more with the same 96 Liters of process water under the same temperature to remove all water soluble impurities. To the oleoresin obtained 19.25 l of ethanol containing 6% moisture was added and stirred at room temperature for 10 minutes to obtain a homogeneous uniform mixture. The contents of the mixture were allowed to settle and separate. The bottom layer of the solvent was drained and the oleoresin thus obtained was retained in the reactor. The process was repeated two times by adding another 19.25 L of ethanol each time to wash the oleoresin.

Enriched oleoresin (7.76 kg) containing 132.20 g/kg of xanthophylls (13.22% xanthophylls) was obtained with a chemical recovery of 91.13%. The enriched oleoresin thus obtained exhibited a carotenoids profile containing 75.28% trans-lutein, 5.64% trans-zeaxanthin and 17.96% of cis-isomers/epoxides.

EXAMPLE 10

Hydrolysis of the Enriched Oleoresin with Alcoholic Alkali 7.76 kg of the enriched marigold oleoresin obtained in example 9 containing 132.20 g/kg of xanthophylls (13.22% xanthophylls) was homogenised for 10 minutes in a 100 L reactor under continuous stirring at a temperature of 40° C. with either steam or hot water in the jacket of the reactor as heating medium. Ethanolic NaOH was prepared by taking 3.88 kg of NaOH with purity of 95% and dissolving it in 15.0 L of ethanol. The prepared ethanolic NaOH was slowly added into reactor containing the homogenised mass (1:2 volumes of oleoresin). The saponification reaction was carried out at a temperature of 75° C. for 30 minutes. After ensuring the degree of saponification to be more than 99% by HPLC, 31 L of demineralised hot water maintained at a temperature of 70° C. was added to the reacted mass and the stirring was continued for 10 minutes. The diluted saponified marigold oleoresin comprising the carotenoids crystals was filtered in a filter press to recover the crystals. The carotenoids crystals thus obtained were washed with 120 L of additional hot water pumped through the filter press to remove the impurities and bring down the pH of the effluent to neutral around 7.0. The wet crystals were then collected from the filter press and dried in a fluid bed drier at a temperature around 55° C. for 1 hour.

Purified xanthophyll crystals (1062 gms) were obtained and the physical recovery of the final product was 13.68%. The carotenoids crystals obtained contained 91.58% carotenoids (determined by UV-Visible spectrophotometer) of which 93.33% was all trans-lutein, 5.62% all trans-zeaxanthin, 0.24% beta carotene and 0.46% cryptoxanthin and without any traces of cis-luteins and epoxides (determined by HPLC). The carotenoids crystals thus obtained, contained 8.00% w/w wax content when measured using Gas-chromatography. The chemical recovery of the final product was 94.80%. The final product contained a moisture content of 0.42% and could not be detected for any traces of residual solvents by gas chromatography analysis.

EXAMPLE 11

Extraction of Marigold Meal with Ethanol and Enrichment in Ethanol

A) Extraction of Lutein Marigold Meal with Alcohol Ethanol 12.5 kg of lutein rich Marigold meal having 8.99 gm/Kg (0.89%) of total carotenoids (with a carotenoids profile of 74.58% trans-lutein, 4.28% trans-zeaxanthin, 1.94% of beta-carotene, 1.02% of cryptoxanthin and 18.08% cis-isomers & epoxides measured by HPLC) was taken in a 200 Liters capacity extractor with circulation facility. 125 Liters of ethanol with a Gas chromatographic purity more than 99% having moisture content less than 1.0% was added to the extractor and circulated. The temperature was raised to 75° C. and maintained for 1 hour under circulation. After 1 hour the extract was drained and collected in a miscella tank. The extraction was repeated for two more times with the same volume of ethanol 125 Liters each under the same conditions of temperature and time. The extracts obtained were collected in the miscella tank. 325 Liters of miscella collected from the three extractions was taken to an evaporator, preferably a falling film evaporator or a wiped film evaporator to obtain a concentrated miscella containing 70% solids and 30% solvent. The concentrated miscella was distilled further in a distillation unit under atmospheric pressure to increase the concentration of solids to 95% with a solvent level of around 5%. The solvent was distilled under reduced pressure (450 to 600 mm Hg) to reduce the solvent level to less than 1%. The total amount of solvent recovered was 262 Liters with a Gas chromatographic purity of more than 99% and with a moisture level of 2%. 2.55 kg of oleoresin containing 39.43 g/kg of total carotenoids (3.943% carotenoids) was obtained with a carotenoids chemical recovery of 89.47%. The lutein chemical recovery was 95.17%. The Marigold oleoresin rich in lutein thus obtained exhibited a carotenoids profile containing 79.33% trans-lutein, 4.24% trans-zeaxanthin and 15.53% of cis-isomers/epoxides 0.18% of beta-carotene, 0.53% of cryptoxanthin, determined by HPLC.

B) Enrichment of Lutein Rich Marigold Oleoresin Using Ethanol.

2.55 kg of lutein rich Marigold oleoresin containing 39.43 g/kg of total carotenoids, obtained from step A), was homogenized at 45° C. with 12.75 Liters of process water in a vessel for 15 minutes. The content of the mixture was allowed to settle and separate. The separated mixture was filtered under vacuum. The Marigold oleoresin thus obtained on the filter was transferred into the vessel. This process was repeated once more with the same 12.75 Liters of process water under the same temperature to remove all water soluble impurities. To the oleoresin obtained 5.0 Liters of ethanol with moisture content about 8% is added and stirred at ambient for 10 to 15 minutes. The content of the mixture was allowed to settle and separate. The top layer of ethanol was decanted and drained. The washes with ethanol are repeated three more times by adding 5.0 Liters of ethanol each time to enrich the oleoresin. 0.695 kg of enriched oleoresin containing 125.09 g/kg of total carotenoids (12.509% carotenoid) was obtained with a carotenoids chemical recovery of 86.46%. The enriched oleoresin rich in lutein thus obtained exhibited a carotenoids profile containing 80.71% trans-lutein, 3.79% trans-zeaxanthin, 0.21% beta-carotene, 0.61% of cryptoxanthin and 14.63% of cis-isomers/epoxides, determined by HPLC.

EXAMPLE 12

Extraction of Zeaxanthin Rich Marigold Meal in Ethanol and Enrichment in Ethanol A) Extraction of Zeaxanthin Rich Marigold Meal with Ethanol:

20 kg of zeaxanthin rich Marigold meal (obtained from Ball Horticulture Inc covered by the U.S. Pat. No. 6,784,351) having 3.29 g/kg (0.329%) of total carotenoids with a carotenoid profile of 59.08% trans-zeaxanthin, 14.80% of betacarotene, 11.77% of trans-lutein, 2.76% of alpha-cryptoxanthin, 2.33% of beta-cryptoxanthin, 1.98% of alpha-carotene, 0.82% of cis-lutein, 0.22% of chrysanthemaxanthin and 6.24% of other unidentified carotenoids, determined by HPLC was taken in a 200 Liters capacity extractor with circulation facility. 120 Liters of ethanol with a Gas chromatographic purity more than 99% with moisture content less than 5% was added to the extractor and circulated. The temperature was raised to 75° C. and maintained for 1 hour under circulation. After 1 hour the extract was drained and collected in a miscella tank. The extraction was repeated for 3 more times each with 60 Liters of ethanol under the same conditions of temperature and time. The extracts obtained were collected in the miscella tank. 260.2 Liters of miscella collected from the above 4 extractions was taken to an evaporator, preferably a falling film evaporator or a wiped film evaporator to obtain a concentrated miscella containing 70% solids and 30% solvent. The concentrated miscella was distilled further in a distillation unit under atmospheric pressure to increase the concentration of solids to 95% with a solvent level of around 5%. The solvent was distilled under reduced pressure (450 to 600 mm Hg) to reduce the solvent level to less than 1%. The total amount of solvent recovered was 224 Liters with a gas chromatographic purity of more than 99% with a moisture level of 5.5%. 9.26 kg of oleoresin containing 6.79 g/kg of total carotenoids (0.679% carotenoids) was obtained with a recovery of 95.55%. The zeaxanthin chemical recovery was 85.49%. The Marigold oleoresin rich in trans-zeaxanthin thus obtained exhibited a carotenoids profile containing 52.86% of trans-zeaxanthin, 9.49% of betacarotene, 13.08% of trans-lutein, 7.75% of alpha-cryptoxanthin, 3.28% of beta-cryptoxanthin, 2.87% of alpha-carotene, 3.93% of cis-lutein and 0.97% of chrysanthemaxanthin and 5.39% of other unidentified carotenoids, determined by HPLC.

B) Enrichment of Zeaxanthin Rich Marigold Oleoresin Using Ethanol.

7.25 kg of the zeaxanthin rich Marigold oleoresin obtained from step A) was taken containing 6.79 g/kg of carotenoids, obtained by extraction with ethanol was homogenized with 22.0 Liters of process water at 45° C. in a vessel for 15 minutes. The contents of the mixture were allowed to settle and separate. The separated mixture was filtered under vacuum. The Marigold oleoresin thus obtained on the filter was transferred into the vessel. This process was repeated once more with the same 22.0 Liters of process water under the same temperature to remove all water soluble impurities. To the oleoresin obtained 7.25 Liters of ethanol with moisture content about 8% is added and stirred at 45° for 10 to 15 minutes. The contents of the mixture were allowed to settle and separate. The top layer of Ethanol was decanted and drained. The washes with ethanol are repeated two more times by adding 7.25 Liters of ethanol each time. 0.948 kg of enriched oleoresin containing 46.98 g/kg of total carotenoids (4.698% carotenoids) was obtained with a carotenoids chemical recovery of 90.48%. The zeaxanthin chemical recovery was 92.28%. The enriched Marigold oleoresin rich in trans-zeaxanthin thus obtained exhibited a carotenoids profile containing 53.99% of trans-zeaxanthin, 10.02% of betacarotene, 15.03% of trans-lutein, 8.25% of alpha-cryptoxanthin, 2.42% of beta-cryptoxanthin, 1.90% of alpha-carotene, 4.28% of cis-lutein and 0.1% of chrysanthemaxanthin and 3.99% of other unidentified carotenoids, determined by HPLC.

EXAMPLE 13

Isolation and Purification to Obtain Carotenoid Crystals Rich in Lutein and Zeaxanthin in the Weight Ratio of about 10:1

The enriched lutein rich Marigold oleoresin obtained from example 11 and the enriched zeaxanthin rich Marigold oleoresin obtained from example 12 are blended in the ratio of 88:12 by physical weight, respectively. 0.3 kg of blended Marigold oleoresin containing 114.32 g/kg of total carotenoids (11.43% carotenoids) was homogenized for 10 minutes in a 5.0 Liters capacity 3 necked round bottom flasks under continuous stirring at a temperature of 40° C. in a hot water bath. Alcoholic KOH was prepared by taking 120 g of KOH (40% calculated to the input oleoresin) with the purity of 90% and dissolving it in 0.45 Liters (1:1.5 volumes to the oleoresin) of ethanol. The prepared alcoholic KOH was slowly added into reaction vessel containing the homogenized Marigold oleoresin. The saponification reaction was carried out at a temperature of 75° C. for 30 minutes. After ensuring the degree of saponification to be more than 99% by HPLC, 1.2 Liters (1:4 volumes calculated to the Oleoresin) of demineralised hot water maintained at a temperature of 75° C. was added to the saponified Marigold oleoresin and stirring was continued for 10 minutes. The diluted saponified mixture with carotenoids crystal was filtered in a buchner funnel to recover the carotenoids crystals. The carotenoids crystal thus obtained were washed with 2.4 Liters (1:8 volumes calculated to the oleoresin) of hot water maintained at a temperature of 75° C. to remove the impurities and bring down the pH of the effluent to neutral around 7.0. The wet crystals (70.2 g) are recovered from the filter and transferred into the vessel. 0.21 liters of ethanol (1:3 volumes to the wet crystals) is added to the vessel and stirred for 10 minutes at a temperature maintained at 50° C. The solution is then filtered through buchner funnel. The wet crystals were then collected from the filter and dried in a Fluid bed drier at a temperature of around 55° C. for 1 hour or until the moisture level is brought to less than 0.3% and the ethanol level is less than 100 ppm.

26.62 g of purified carotenoids crystals rich in trans-lutein and trans-zeaxanthin were obtained and the physical recovery of the final product was 8.63%. The carotenoids crystals obtained contained 89.52% total carotenoids by weight determined by UV-Visible spectrophotometer of which 89.91% was all trans-lutein, 9.03% all trans-zeaxanthin, 0.37% beta-cryptoxanthin, and 0.06% of beta-carotene and without any traces of cis-luteins and epoxides, determined by HPLC.

The carotenoids crystals thus obtained contain 80.48% of trans-lutein by weight and 8.08% by weight of trans-zeaxanthin with the ratio of trans-Lutein to trans-zeaxanthin by weight to be at about 10: 1 ratio (9.95).

The carotenoid crystals thus obtained contained 10.40% of wax content when measured using Gas Chromatography. The carotenoids chemical recovery of the final product was 69.49% with a lutein chemical recovery of 78.71% and a zeaxanthin chemical recovery of 86.22%. The final product contained a moisture content of 0.22% with 58.82 ppm of ethanol.

EXAMPLE 14

Isolation and Purification to Obtain Carotenoid Crystals Rich in Lutein and Zeaxanthin in the Ratio of About 5:1

The enriched lutein rich Marigold oleoresin obtained from example 11 and the enriched zeaxanthin rich Marigold oleoresin obtained from example 12 are blended in the ratio of 70:30 by physical weight, respectively. 0.3 kg of blended Marigold oleoresin containing 101.86/kg of total carotenoids (10.18% carotenoids) was homogenized for 10 minutes in a 5.0 Liters capacity 3 necked round bottom flasks under continuous stirring at a temperature of 40° C. in a hot water bath. Alcoholic KOH was prepared by taking 120 g of KOH (40% calculated to the input oleoresin) with the purity of 90% and dissolving it in 0.45 Liters (1:1.5 volumes to the oleoresin) of ethanol. The prepared alcoholic KOH was slowly added into reaction vessel containing the homogenized Marigold oleoresin. The saponification reaction was carried out at a temperature of 75° C. for 30 minutes. After ensuring the degree of saponification to be more than 99% by HPLC, 1.2 Liters (1:4 volumes calculated to the oleoresin) of demineralised hot water maintained at a temperature of 75° C. was added to the saponified Marigold oleoresin and stirring was continued for 10 minutes. The diluted saponified mixture with carotenoids crystal was filtered in a Buchner funnel to recover the carotenoids crystals. The carotenoids crystal thus obtained were washed with 2.4 Liters (1:8 volumes calculated to the oleoresin) of hot water maintained at a temperature of 75° C. to remove the impurities and bring down the pH of the effluent to neutral around 7.0. The wet crystals (78.5 g) are recovered from the filter and transferred into the vessel. 0.23 liters of ethanol (1:3 volumes to the wet crystals) is added to the vessel and stirred for 10 minutes at a temperature maintained at 50° C. The solution is then filtered through Buchner funnel. The wet crystals were then collected from the filter and dried in a fluid bed drier at a temperature of around 55° C. for 1 hour or until the moisture level is brought to less than 0.3% and the ethanol level is less than 100 ppm.

21.59 g of purified carotenoids crystals rich in lutein and zeaxanthin were obtained and the physical recovery of the final product was 7.19%. The carotenoid crystals obtained contained 91.39% total carotenoids by weight determined by UV-Visible spectrophotometer of which 82.64% was all trans-lutein, 16.29% all trans-zeaxanthin, 0.70% beta-cryptoxanthin, and 0.10% of beta-carotene and without any traces of cis-luteins and epoxides, determined by HPLC.

The carotenoids crystals thus obtained contain 75.52% of trans-lutein by weight and 14.88% by weight of trans-zeaxanthin with the ratio of trans-lutein to trans-zeaxanthin by weight to be at about 5:1 ratio (5.07).

The carotenoids crystals thus obtained contained 8.46% of wax content when measured using Gas Chromatography. The carotenoids chemical recovery of the final product was 64.61% with a lutein chemical recovery of 69.12% and a zeaxanthin chemical recovery of 76.22%. The final product contained a moisture content of 0.28% with 23.30 ppm of ethanol.

EXAMPLE 15

Isolation and Purification to Obtain Carotenoids Crystals Rich in Lutein and Zeaxanthin in the Ratio of About 1:1

The enriched lutein rich marigold oleoresin obtained from example 11 and the enriched zeaxanthin rich marigold oleoresin obtained from example 12 are blended in the ratio of 18:82 by weight, respectively. 0.3 kg of blended marigold oleoresin containing 62.24/kg of total carotenoids (6.22% carotenoids) was homogenized for 10 minutes in a 5.0 litters capacity 3 necked round bottom flask under continuous stirring at a temperature of 40° C. in a hot water bath. Alcoholic KOH was prepared by taking 120 g of KOH (40% calculated to the input oleoresin) with the purity of 90% and dissolving it in 0.45 liters (1:1.5 volumes to the oleoresin) of ethanol. The prepared alcoholic KOH was slowly added into reaction vessel containing the homogenized marigold oleoresin. The saponification reaction was carried out at a temperature of 75° C. for 30 minutes. After ensuring the degree of saponification to be more than 99% by HPLC, 1.2 litters (1:4 volumes calculated to the oleoresin) of demineralised hot water maintained at a temperature of 75° C. was added to the saponified marigold oleoresin and stirring was continued for 10 minutes. The diluted Saponified mixture with carotenoids crystal was filtered in a Buchner funnel to recover the carotenoid crystals. The carotenoids crystal thus obtained were washed with 2.4 Liters (1:8 volumes calculated to the Oleoresin) of hot water maintained at a temperature of 75° C. to remove the impurities and bring down the pH of the effluent to neutral around 7.0. The wet crystals (62.2 g) are recovered from the filter and transferred into the vessel. 0.18 liters of ethanol (1:3 volumes to the wet crystals) is added to the vessel and stirred for 10 minutes at a temperature maintained at 50° C. The solution is then filtered through Buchner funnel. The wet crystals were then collected from the filter and dried in a fluid bed drier at a temperature of around 55° C. for 1 hour or until the moisture level is brought to less than 0.3% and the ethanol level is less than 100 ppm.

11.28 g of purified carotenoids crystals rich in trans-lutein and trans-zeaxanthin were obtained and the physical recovery of the final product was 3.76%. The carotenoids crystals obtained contained 92.34% total carotenoids by weight determined by UV-Visible spectrophotometer of which 48.52% was all trans-lutein, 46.38% all trans-zeaxanthin, 1.22% Beta-cryptoxanthin, and 2.30% of beta-carotene and without any traces of cis-luteins and epoxides, determined by HPLC.

The carotenoids crystals thus obtained contain 44.80% of trans-lutein by weight and 42.82% by weight of trans-zeaxanthin with the ratio of trans-lutein to trans-zeaxanthin by weight to be at about 1:1 ratio (1.04).

The carotenoid crystals thus obtained contained 7.42% of wax content when measured using Gas Chromatography. The carotenoids chemical recovery of the final product was 55.82% with a Lutein chemical recovery of 62.86% and a zeaxanthin chemical recovery of 69.33%. The final product contained a moisture content of 0.27% with 35.55 ppm of ethanol.

EXAMPLE 16

Extraction of Lutein Rich Marigold Meal with Isopropyl Alcohol and Enrichment in Ethanol A) Extraction of Lutein Rich Marigold Meal with Iso Propyl Alcohol 12.5 kg of Lutein rich Marigold Meal having 8.99 gm/Kg (0.89%) of total carotenoids (with a carotenoids profile of 74.58% trans-Lutein, 4.28% trans-Zeaxanthin, 1.94% of Beta-carotene, 1.02% of Cryptoxanthin and 18.08% cis-isomers & epoxides, measured by HPLC) was taken in a 125 Liters capacity extractor with circulation facility. 75 Liters of Iso-propyl alcohol with a Gas chromatographic purity more than 99% with less than 1% moisture content was added to the extractor and circulated. The temperature was raised to 55° C. and maintained for 1 hour under circulation. After 1 hour the extract was drained and collected in a tank. The extraction was repeated for two more times each with 75 Liters of Iso-propyl alcohol under the same conditions of temperature and time. The extracts obtained were collected in the miscella tank. The fourth and fifth extractions were carried out using 62.5 Liters of iso-propyl alcohol in each extraction under circulation and at a temperature of 58° C. 325 Liters of miscella collected from the five extractions was taken to an evaporator, preferably a falling film evaporator or a wiped film evaporator to obtain a concentrated miscella containing 70% solids and 30% solvent. The concentrated miscella was distilled further in a distillation unit under atmospheric pressure to increase the concentration of solids to 95% with a solvent level of around 5%. The solvent was distilled under reduced pressure (450 to 600 mm Hg) to reduce the solvent level to less than 1%. The total amount of solvent recovered was 295 Liters with a Gas chromatographic purity of more than 99% 2.0 kg of oleoresin containing 51.28 g/kg of total carotenoids (5.12% carotenoids) was obtained with a carotenoids chemical recovery of 91.26%. The lutein chemical recovery was 87.23%. The Marigold oleoresin rich in lutein thus obtained exhibited a carotenoids profile containing 71.28% trans-lutein, 5.83% trans-zeaxanthin, 1.92% of Beta-carotene, 1.53% of cryptoxanthin and 19.36% of cis-isomers/epoxides determined by HPLC.

B) Enrichment of Lutein Rich Marigold Oleoresin Using Ethanol.

2.0 kg of lutein rich Marigold oleoresin containing 51.28 g/kg of total carotenoids, obtained from step A), was homogenized at room temperature with 2.0 Liters of ethanol in a vessel for 10 minutes to obtain a homogeneous uniform mixture. The contents of the mixture were allowed to settle and separate. The bottom layer of the solvent was drained and the oleoresin thus obtained was retained in the vessel. The process was repeated for two more times by adding 2.0 Liters of ethanol each time to enrich the oleoresin. 0.672 kg of enriched oleoresin containing 142.8 g/kg of total carotenoids (14.28% carotenoids) was obtained with a carotenoids chemical recovery of 93.56%. The enriched oleoresin rich in lutein thus obtained exhibited a carotenoids profile containing 73.22% trans-lutein, 4.90% trans-zeaxanthin, 1.62% of beta-carotene, 0.79% of cryptoxanthin and 19.38% of cis-isomers/epoxides, determined by HPLC.

EXAMPLE 17

Extraction of Zeaxanthin Rich Marigold Meal with Isopropyl Alcohol and Enrichment in Ethanol A) Extraction Zeaxanthin Rich Marigold Meal in Isopropyl Alcohol:

20 kg of zeaxanthin rich Marigold meal (Obtained from Ball Horticulture Inc covered by the U.S. Pat. No. 6,784,351) having 3.29 g/kg (0.329%) of total carotenoids with a carotenoid profile of 59.08% trans-zeaxanthin, 14.80% of betacarotene, 11.77% of trans-lutein, 2.76% of alpha-cryptoxanthin, 2.33% of beta-cryptoxanthin, 1.98% of alpha-carotene, 0.82% of cis-lutein, 0.22% of chrysanthemaxanthin and 6.24% of other unidentified carotenoids, measured by HPLC, was taken in a 200 Liters capacity extractor with circulation facility.

120 Liters of Isopropyl alcohol with a Gas chromatographic purity more than 99% with less than 1% moisture content was added to the extractor and circulated. The temperature was raised to 55° C. and maintained for 1 hour under circulation. After 1 hour the extract was drained and collected in a miscella tank. The extraction was repeated for 2 more times each with 60 Liters of Isopropyl alcohol under the same conditions of temperature and time. The extracts obtained were collected in the miscella tank. 217.2 Liters of miscella collected from the above 3 extractions was taken to an evaporator, preferably a falling film evaporator or a wiped film evaporator to obtain a concentrated miscella containing 70% solids and 30% solvent. The concentrated miscella was distilled further in a distillation unit under atmospheric pressure to increase the concentration of solids to 95% with a solvent level of around 5%. The solvent was distilled under reduced pressure (450 to 600 mm Hg) to reduce the solvent level to less than 1%. The total amount of solvent recovered was 188 Liters with a Gas chromatographic purity of more than 99%.

3.252 kg of oleoresin containing 20.04 g/kg of total carotenoids (2.004% carotenoids) was obtained with a recovery of 99.04%. The zeaxanthin chemical recovery was 92.75%. The Marigold oleoresin rich in trans-zeaxanthin thus obtained exhibited a carotenoids profile containing 53.74% of trans-zeaxanthin, 14.51% of betacarotene, 15.15% of trans-lutein, 3.64% of Alpha-cryptoxanthin, 2.26% of Beta-cryptoxanthin, 3.11% of alpha-carotene, 1.60% of cis-lutein and 0.52% of chrysanthemaxanthin and 5.47% of other unidentified carotenoids, determined by HPLC.

B) Enrichment of Zeaxanthin Rich Marigold Oleoresin Using Ethanol.

2.31 kg of zeaxanthin rich Marigold oleoresin containing 20.04 g/kg of carotenoids, obtained from step A) was homogenized at 45° C. with 10.8 Liters of process water in a vessel for 15 minutes. The contents of the mixture were allowed to settle and separate. The separated mixture was filtered under vacuum. The Marigold oleoresin thus obtained on the filter was transferred into the vessel. This process was repeated once more with the same 10.8 Liters of process water under the same temperature to remove all water soluble impurities. To the oleoresin obtained 5.4 Liters of ethanol with moisture content of about 5% is added and stirred at 45° for 10 to 15 minutes. The content of the mixture was allowed to settle and separate. The top layer of ethanol was decanted and drained. The washes with Ethanol are repeated two more times by adding 4.2 Liters of ethanol each time. 0.969 kg of enriched oleoresin containing 40.83 g/kg of total carotenoids (4.083% carotenoids) was obtained with a carotenoids chemical recovery of 85.47%. The zeaxanthin chemical recovery was 88.88%. The enriched Marigold Oleoresin rich in trans-zeaxanthin thus obtained exhibited a carotenoids profile containing 55.89% of trans-zeaxanthin, 13.62% of betacarotene, 16.63% of trans-lutein, 3.57% of alpha-cryptoxanthin, 2.27% of beta-cryptoxanthin, 3.72% of alpha-carotene, 0.71% of cis-lutein and 0.25% of chrysanthemaxanthin and 3.34% of other unidentified carotenoids, determined by HPLC.

EXAMPLE 18

Isolation and Purification to Obtain Carotenoid Crystals Rich in Trans-Lutein and Trans-Zeaxanthin in the Weight Ratio of About 10:1

The enriched lutein rich Marigold oleoresin obtained in example 16 and the enriched zeaxanthin rich Marigold oleoresin obtained in example 17 are blended in the ratio of 86:14 by physical weight, respectively. 0.3 kg of blended Marigold oleoresin containing 129.20 g/kg of total carotenoids 12.92% carotenoids) was homogenized for 10 minutes in a 5.0 Liters capacity 3 necked round bottom flask under continuous stirring at a temperature of 40° C. in a hot water bath. Alcoholic KOH was prepared by taking 120 g of KOH (40% calculated to the input oleoresin) with the purity of 90% and dissolving it in 0.45 Liters (1:1.5 volumes to the oleoresin) of ethanol. The prepared alcoholic KOH was slowly added into reaction vessel containing the homogenized Marigold oleoresin. The saponification reaction was carried out at a temperature of 75° C. for 30 minutes. After ensuring the degree of saponification to be more than 99% by HPLC, 1.2 Liters (1:4 volumes calculated to the oleoresin) of demineralised hot water maintained at a temperature of 75° C. was added to the saponified Marigold oleoresin and stirring was continued for 10 minutes. The diluted saponified mixture with carotenoids crystal was filtered in a buchner funnel to recover the carotenoid crystals. The carotenoids crystal thus obtained was washed with 2.4 Liters (1:8 volumes calculated to the oleoresin) of hot water maintained at a temperature of 75° C. to remove the impurities and bring down the pH of the effluent to neutral around 7.0. The wet crystals were then collected from the filter and dried in a Fluid bed drier at a temperature of around 55° C. hour or until the moisture level is brought to less than 0.3% and the isopropyl alcohol and ethanol levels are less than 100 ppm each.

35.59 g of Purified carotenoids crystals rich in trans-lutein and trans-zeaxanthin were obtained and the physical recovery of the final product was 11.86%. The carotenoid crystals obtained contained 91.22% total carotenoids by weight determined by UV-Visible spectrophotometer of which 89.84% was all trans-lutein, 9.04% all trans-zeaxanthin, 0.43% beta-cryptoxanthin, and 0.37% of beta-carotene and without any traces of cis-luteins and epoxides, determined by HPLC.

The carotenoids crystals thus obtained contain 82.10% of trans-lutein by weight and 8.26% by weight of trans-zeaxanthin with the ratio of trans-lutein to trans-zeaxanthin by weight to be at about 10:1 ratio (9.94).

The carotenoid crystals thus obtained contained 8.62% of wax content when measured using Gas Chromatography. The carotenoids chemical recovery of the final product was 83.76% with a Lutein chemical recovery of 92.78% and a zeaxanthin chemical recovery of 95.26%. The final product contained a moisture content of 0.51% with 32.3 ppm of ethanol, 22.5 ppm of Isopropyl alcohol detected by Gas chromatography.

EXAMPLE 19

Isolation and Purification to Obtain Carotenoid Crystals Rich in Lutein and Zeaxanthin in the Ratio of About 5:1

The enriched lutein rich Marigold oleoresin obtained from example 16 and the enriched zeaxanthin rich Marigold oleoresin obtained from example 17 are blended in the ratio of 60:40 by physical weight, respectively. 0.30 kg of blended Marigold oleoresin containing 103.50 g/kg of total carotenoids 10.35% carotenoids) was homogenized for 10 minutes in a 5.0 Liters capacity 3 necked round bottom flask under continuous stirring at a temperature of 40° C. in a hot water bath. Alcoholic KOH was prepared by taking 120 g of KOH (40% calculated to the input oleoresin) with the purity of 90% and dissolving it in 0.45 Liters (1:1.5 volumes to the oleoresin) of ethanol. The prepared alcoholic KOH was slowly added into reaction vessel containing the homogenized Marigold oleoresin. The saponification reaction was carried out at a temperature of 75° C. for 30 minutes. After ensuring the degree of saponification to be more than 99% by HPLC, 1.2 Liters (1:4 volumes calculated to the oleoresin) of demineralised hot water maintained at a temperature of 75° C. was added to the saponified marigold oleoresin and stirring was continued for 10 minutes. The diluted Saponified mixture with carotenoids crystal was filtered in a buchner funnel to recover the carotenoid crystals. The carotenoids crystal thus obtained were washed with 2.4 Liters (1:8 volumes calculated to the Oleoresin) of hot water maintained at a temperature of 75° C. to remove the impurities and bring down the pH of the effluent to neutral around 7.0. The wet crystals (83.2 g) are recovered from the filter and Transferred into the vessel. 0.25 liters of ethanol (1:3 volume to the wet crystals) is added to the vessel and stirred for 10 minutes at a temperature maintained at 50° C. The solution is then filtered through buchner funnel. The wet crystals were then collected from the filter and dried in a Fluid bed drier at a temperature of around 55° C. for 1 hour or until the moisture level is brought to less than 0.3% and the isopropyl alcohol and Ethanol levels is less than 100 ppm each.

22.95 g of purified carotenoids crystals rich in trans-lutein and trans-zeaxanthin were obtained and the physical recovery of the final product was 7.65%. The carotenoid crystals obtained contained 91.86% total carotenoids by weight determined by UV-Visible spectrophotometer of which 82.23% was all trans-lutein, 16.78% all trans-zeaxanthin, 0.57% beta-cryptoxanthin, and 0.40% of beta-carotene and without any traces of cis-luteins and epoxides, determined by HPLC.

The carotenoids crystals thus obtained contain 73.56% of trans-lutein by weight and 15.01% by weight of trans-zeaxanthin with the ratio of trans-lutein to trans-zeaxanthin by weight to be at about 5:1 ratio (4.9).

The carotenoid crystals thus obtained contained 8.04% of wax content when measured using Gas Chromatography. The carotenoids chemical recovery of the final product was 67.89%, with lutein chemical recovery of 84.64% and 85.48% of zeaxanthin. The final product contained a moisture content of 0.29% with 63.2 ppm of ethanol and 13.05 ppm of Isopropyl alcohol detected by Gas chromatography.

EXAMPLE 20

Isolation and Purification to Obtain Carotenoids Crystals Rich in Lutein and Zeaxanthin in the Ratio of About 1:1

The enriched lutein rich Marigold oleoresin obtained in example 16 and the enriched zeaxanthin rich Marigold oleoresin obtained in example 17 are blended in the ratio of 14:86 by physical weight, respectively. 0.30 kg of blended Marigold oleoresin containing 56.13 g/kg of total carotenoids (5.613% carotenoids) was homogenized for 10 minutes in a 5.0 Liters capacity 3 necked round bottom flask under continuous stirring at a temperature of 40° C. in a hot water bath. Alcoholic KOH was prepared by taking 120 g of KOH (40% calculated to the input oleoresin) with the purity of 90% and dissolving it in 0.45 Liters (1:1.5 volumes to the oleoresin) of ethanol. The prepared alcoholic KOH was slowly added into reaction vessel containing the homogenized Marigold oleoresin. The saponification reaction was carried out at a temperature of 75° C. for 30 minutes. After ensuring the degree of saponification to be more than 99% by HPLC, 1.2 Liters (1:4 volumes calculated to the oleoresin) of demineralised hot water maintained at a temperature of 75° C. was added to the saponified Marigold oleoresin and stirring was continued for 10 minutes. The diluted saponified mixture with carotenoids crystal was filtered in a buchner funnel to recover the carotenoids crystals. The carotenoids crystal thus obtained were washed with 2.4 Liters (1:8 volumes calculated to the oleoresin) of hot water maintained at a temperature of 75° C. to remove the impurities and bring down the pH of the effluent to neutral around 7.0. The wet crystals (25.2 g) are recovered from the filter and transferred into the vessel. 0.075 liters of ethanol (1:3 volume to the wet crystals) is added to the vessel and stirred for 10 minutes at a temperature maintained at 50° C. The solution is then filtered through buchner funnel. The wet crystals were then collected from the filter and dried in a Fluid bed drier at a temperature of around 55° C. for 1 hour or until the moisture level is brought to less than 0.3% and the Isopropyl alcohol and ethanol levels is less than 100 ppm each.

9.69 g of purified carotenoids crystals rich in trans-lutein and trans-zeaxanthin were obtained and the physical recovery of the final product was 3.23%. The carotenoids crystals obtained contained 90.98% total carotenoids by weight determined by UV-Visible spectrophotometer of which 48.78% was all trans-lutein, 49.87% all trans-zeaxanthin, 0.42% beta-cryptoxanthin, and 0.93% of beta-carotene and without any traces of cis-luteins, chrysanthemaxanthin, alpha-cryptoxanthin, alpha-carotene and epoxides, determined by HPLC.

The carotenoids crystals thus obtained contain 43.73% of trans-lutein by weight and 44.70% by weight of trans-zeaxanthin with the ratio of trans-lutein to trans-zeaxanthin by weight to be at about 1:1 ratio (0.978).

The carotenoids crystals thus obtained contained 8.99% of wax content when measured using Gas Chromatography. The carotenoids chemical recovery of the final product was 52.38% with a lutein chemical recovery of 65.58% and a zeaxanthin chemical recovery of 76.19%. The final product contained a moisture content of 0.28% with 12.08 ppm of ethanol and 35.06 ppm of isopropyl alcohol detected by Gas chromatography.

EXAMPLE 21

Extraction, Isolation and Purification of Carotenoids Crystals Rich in Lutein and Zeaxanthin from Marigold Meals Using Ethanol as Solvent for Extraction Followed by Crystal Blending A) Extraction of Lutein Rich Marigold Meal in Ethanol and Enrichment of Lutein Rich Marigold Oleoresin Using Ethanol.

100 kg of lutein rich Marigold meal having 8.99 gm/Kg (0.89%) of total carotenoids (with a carotenoids profile of 74.58% trans-lutein, 4.28% trans-zeaxanthin, 1.94% of beta-carotene, 1.02% of cryptoxanthin and 18.08% cis-isomers & epoxides measured by HPLC) was taken in a 2 KL capacity extractor with circulation facility. 1000 Liters of ethanol with a Gas chromatographic purity more than 99% having moisture content less than 1.0% was added to the extractor and circulated. The temperature was raised to 75° C. and maintained for 1 hour under circulation. After 1 hour the extract was drained and collected in a tank. The extraction was repeated for two more times with the same volume of ethanol 1000 Liters each under the same conditions of temperature and time. The extracts obtained were collected in the miscella tank. 2600 Liters of miscella collected from the three extractions was taken to an evaporator, preferably a falling film evaporator or a wiped film evaporator to obtain a concentrated miscella containing 70% solids and 30% solvent. The concentrated miscella was distilled further in a distillation unit under atmospheric pressure to increase the concentration of solids to 95% with a solvent level of around 5%. The solvent was distilled under reduced pressure (450 to 600 mm Hg) to reduce the solvent level to less than 1%. The total amount of solvent recovered was 2104 Liters with a Gas chromatographic purity of more than 99% and with a moisture level of 2%. 20.4 kg of oleoresin containing 40.02 g/kg of total carotenoids (4.0% carotenoids) was obtained with a carotenoids chemical recovery of 91.73%. The lutein chemical recovery was 97.43%. The Marigold oleoresin rich in lutein thus obtained exhibited a carotenoids profile containing 79.22% trans-lutein, 4.18% trans-zeaxanthin and 16.13% of cis-isomers/epoxides 0.22% of beta-carotene, 0.25% of cryptoxanthin, determined by HPLC.

18.36 kg of lutein rich Marigold oleoresin containing 40.02/kg of total carotenoids, obtained from above step 1 (a) was homogenized at 45° C. with 92 Liters of process water in a vessel for 15 minutes. The content of the mixture was allowed to settle and separate. The separated mixture was filtered under vacuum. The Marigold oleoresin thus obtained on the filter was transferred into the vessel. This process was repeated once more with the same 92 Liters of process water under the same temperature to remove all water soluble impurities. To the oleoresin obtained 36 Liters of ethanol with moisture content about 8% is added and stirred at ambient for 10 to 15 minutes. The content of the mixture was allowed to settle and separate. The top layer of ethanol was decanted and drained. The washes with ethanol are repeated three more times by adding 36 Liters of ethanol each time to enrich the oleoresin. 5.24 kg of enriched oleoresin containing 124.39 g/kg of total carotenoids (12.44% carotenoids) was obtained with a carotenoids chemical recovery of 88.71%. The enriched oleoresin rich in lutein thus obtained exhibited a carotenoids profile containing 79.83% trans-lutein, 4.02% trans-zeaxanthin, 0.23% beta-carotene, 0.56% of cryptoxanthin and 15.36% of cis-isomers/epoxides, determined by HPLC.

B) Extraction of Zeaxanthin Rich Marigold Meal in Ethanol and Enrichment in Ethanol 44 kg of zeaxanthin rich Marigold meal (obtained from Ball Horticulture Inc covered by the U.S. Pat. No. 6,784,351) having 3.29 g/kg (0.329%) of total carotenoids with a carotenoid profile of 59.08% trans-zeaxanthin, 14.80% of betacarotene, 11.77% of trans-lutein, 2.76% of alpha-cryptoxanthin, 2.33% of beta-cryptoxanthin, 1.98% of alpha-carotene, 0.82% of cis-lutein, 0.22% of chrysanthemaxanthin and 6.24% of other unidentified carotenoids, determined by HPLC was taken in a 500 Liters capacity extractor with circulation facility. 264 Liters of ethanol with a Gas chromatographic purity more than 99% with moisture content less than 5% was added to the extractor and circulated. The temperature was raised to 75° C. and maintained for 1 hour under circulation. After 1 hour the extract was drained and collected in a miscella tank. The extraction was repeated for 3 more times each with 132 Liters of ethanol under the same conditions of temperature and time. The extracts obtained were collected in the miscella tank. 578 Liters of miscella collected from the above 4 extractions was taken to an evaporator, preferably a falling film evaporator or a wiped film evaporator to obtain a concentrated miscella containing 70% solids and 30% solvent. The concentrated miscella was distilled further in a distillation unit under atmospheric pressure to increase the concentration of solids to 95% with a solvent level of around 5%. The solvent was distilled under reduced pressure (450 to 600 mm Hg) to reduce the solvent level to less than 1%. The total amount of solvent recovered was 498 Liters with a gas chromatographic purity of more than 99% with a moisture level of 5.2%. 21.1 kg of oleoresin containing 6.63 g/kg of total carotenoids (0.663% carotenoids) was obtained with a recovery of 96.63%. The zeaxanthin chemical recovery was 87.02%. The Marigold oleoresin rich in trans-zeaxanthin thus obtained exhibited a carotenoids profile containing 53.20% of trans-zeaxanthin, 9.26% of betacarotene, 12.93% of trans-lutein, 6.38% of alpha-cryptoxanthin, 2.38% of beta-cryptoxanthin, 2.66% of alpha-carotene, 3.63% of cis-lutein and 1.23% of chrysanthemaxanthin and 8.33% of other unidentified carotenoids, determined by HPLC.

19.57 kg of the zeaxanthin rich Marigold oleoresin was taken containing 6.63 g/kg of carotenoids, obtained by extraction with ethanol was homogenized with 60.0 Liters of process water at 45° C. in a vessel for 15 minutes. The contents of the mixture were allowed to settle and separate. The separated mixture was filtered under vacuum. The Marigold oleoresin thus obtained on the filter was transferred into the vessel. This process was repeated once more with the same 60.0 Liters of process water under the same temperature to remove all water soluble impurities. To the oleoresin obtained 20 Liters of ethanol with moisture content about 8% is added and stirred at 45° C. for 10 to 15 minutes. The contents of the mixture were allowed to settle and separate. The top layer of ethanol was decanted and drained. The washes with ethanol are repeated two more times by adding 20 Liters of ethanol each time. 2.559 kg of enriched oleoresin containing 46.20 g/kg of total carotenoids (4.62% carotenoids) was obtained with a carotenoids chemical recovery of 91.11%. The zeaxanthin chemical recovery was 90.53%. The enriched Marigold oleoresin rich in trans-zeaxanthin thus obtained exhibited a carotenoids profile containing 52.86% of trans-zeaxanthin, 10.36% of betacarotene, 16.28% of trans-lutein, 7.83% of alpha-cryptoxanthin, 2.33% of beta-cryptoxanthin, 2.10% of alpha-carotene, 4.36% of cis-lutein and 0.08% of chrysanthemaxanthin and 3.8% of other unidentified carotenoids, determined by HPLC.

C) Isolation and Purification to Obtain Carotenoids Crystals Rich in Lutein 4.8 kg of the enriched lutein rich Marigold oleoresin obtained from the above step (A) containing 124.39 g/kg of total carotenoids (12.43% carotenoids) was homogenized for 10 minutes in a 100 Liters capacity extractor under continuous stirring at a temperature of 40° C. maintained by hot water circulation in the jacket. Alcoholic KOH was prepared by taking 1.92 kg of KOH (40% calculated to the input oleoresin) with the purity of 90% and dissolving it in 7.2 Liters (1:1.5 w/v to the oleoresin) of ethanol. The prepared alcoholic KOH was slowly added into reaction vessel containing the homogenized Marigold oleoresin. The saponification reaction was carried out at a temperature of 75° C. for 30 minutes. After ensuring the degree of saponification to be more than 99% by HPLC, 19.2 Liters (1:4 w/v calculated to the Oleoresin) of demineralised hot water maintained at a temperature of 75° C. was added to the saponified Marigold oleoresin and stirring was continued for 10 minutes. The diluted saponified mixture with carotenoids crystal was filtered in a neutch filter to recover the carotenoid crystals. The carotenoids crystal thus obtained were washed with 38.4 Liters (1:8 w/v calculated to the oleoresin) of hot water maintained at a temperature of 75° C. to remove the impurities and bring down the pH of the effluent to neutral around 7.0. The wet crystals (1160 g) are recovered from the filter and transferred into the vessel. 3.48 liters of ethanol (1:3 w/v to the wet crystals) is added to the vessel and stirred for 10 minutes at a temperature maintained at 50° C. The solution is then filtered through neutch filter. The wet crystals were then collected from the neutch filter and dried in a Fluid bed drier at a temperature of around 55° C. for 1 hour or until the moisture level is brought to less than 0.3% and the ethanol level is less than 100 ppm.

504.6 g of purified carotenoids crystals rich in trans-lutein were obtained and the physical recovery of the final product was 10.51%. The carotenoid crystals thus obtained contained 90.83% total carotenoids determined by UV-Visible spectrophotometer of which 92.36% was all trans-Lutein, 5.72% all trans-zeaxanthin, 0.30% of cis-luteins, 0.51% of beta carotene and 1.11% of cryptoxanthin determined by HPLC. The chemical recovery of the final product is 76.76%.

D) Isolation and Purification to Obtain Carotenoids Crystals Rich in Zeaxanthin 2.1 kg of the enriched lutein rich Marigold oleoresin obtained from the above step (C) containing 46.20 g/kg of total carotenoids (4.62% carotenoids) was homogenized for 10 minutes in a 50 Liters capacity extractor under continuous stirring at a temperature of 40° C. maintained by hot water circulation in the jacketed vessel. Alcoholic KOH was prepared by taking 840 g of KOH (40% calculated to the input oleoresin) with the purity of 90% and dissolving it in 3.15 Liters (1:1.5 w/v to the oleoresin) of ethanol. The prepared alcoholic KOH was slowly added into reaction vessel containing the homogenized Marigold oleoresin. The saponification reaction was carried out at a temperature of 75° C. for 30 minutes. After ensuring the degree of saponification to be more than 99% by HPLC, 8.4 Liters (1:4 w/v calculated to the Oleoresin) of demineralised hot water maintained at a temperature of 75° C. was added to the saponified Marigold oleoresin and stirring was continued for 10 minutes. The diluted saponified mixture with carotenoids crystal was filtered in a buchner funnel to recover the carotenoid crystals. The carotenoids crystal thus obtained were washed with 16.8 Liters (1:8 w/v calculated to the oleoresin) of hot water maintained at a temperature of 75° C. to remove the impurities and bring down the pH of the effluent to neutral around 7.0. The wet crystals (475.3 g) are recovered from the filter and transferred into the vessel. 1.42 liters of ethanol (1:3 w/v to the wet crystals) is added to the vessel and stirred for 10 minutes at a temperature maintained at 50° C. The solution is then filtered through Buchner funnel. The wet crystals were then collected from the filter and dried in a Fluid bed drier at a temperature of around 55° C. for 1 hour or until the moisture level is brought to less than 0.3% and the ethanol level is less than 100 ppm.

35.2 g of purified carotenoids crystals rich in trans-Zeaxanthin were obtained and the physical recovery of the final product was 1.67%. The carotenoids crystals thus obtained contained 72.3% total carotenoids determined by UV-Visible spectrophotometer of which 88.60% was all trans-Zeaxanthin, 8.29% all trans-Lutein, 0.21% of Chrysanthemaxanthin, 0.51% of Alphacarotene and 2.39% of beta-carotene and without any traces of cis-luteins and epoxides, determined by HPLC.

The carotenoids crystals thus obtained contain 64.05% of trans-Zeaxanthin by weight and 5.99% by weight of trans-Lutein with a chemical recovery being 26.23% of Total carotenoids.

E) Blending of Lutein Rich Crystals and Zeaxanthin Rich Crystals

The obtained crystals from the step (C) and the crystals obtained from the step (D) are blended in specific ratios in the laboratory mixer blender for 10 minutes or until there is uniformity of color in the final blend. The blended sample is analyzed for its total carotenoids and HPLC profile. All the three blends are blended in the ratio of 10:1 trans-Lutein to trans-zeaxanthin by taking different quantities at each blend. The theoretical profile of the 10:1 blend of trans-Lutein to trans-zeaxanthin would be of 90.12% total carotenoids measured by UV with 89.1% trans-Lutein, 8.91% of trans-zeaxanthin and with 1.97% of other carotenoids, measured by HPLC.

Blend 1: 225 g of Lutein and 9 g of Zeaxanthin is taken and blended as mentioned above. The carotenoids crystals thus obtained contained 90.08% total. carotenoids determined by UV-Visible spectrophotometer of which 88.9% was all trans-Lutein, 9.73% all trans-Zeaxanthin and 1.37% of beta-carotene and other carotenoids without any traces of cis-luteins and epoxides, determined by HPLC. The obtained ratio in the above blend is 9.13.

Blend 2: 150 g of Lutein and 6 g of Zeaxanthin is taken and blended as mentioned above. The carotenoids crystals obtained in blend 2 contained 88.96% total carotenoids determined by UV-Visible spectrophotometer of which 89.46% was all trans-Lutein, 8.59% all trans-Zeaxanthin and 1.95% of beta-carotene and other carotenoids without any traces of cis-luteins and epoxides, determined by HPLC. The obtained ratio in the above blend is 10.41.

Blend 3: 100 g of Lutein and 4 g of Zeaxanthin is taken and blended as mentioned above The carotenoids crystals obtained in blend 3 contained 90.38% total carotenoids determined by UV-Visible spectrophotometer of which 90.63% was all trans-Lutein, 8.14% all trans-Zeaxanthin and 1.23% of beta-carotene and other carotenoids without any traces of cis-luteins and epoxides, determined by HPLC. The obtained ratio in the above blend is 11.13.

It is evident from the above experiment that the crystal blending after purifying individually results in varied ratios of lutein to zeaxanthin like 9.13, 10.41, and 11.13. It is also evident that the recoveries of zeaxanthin purified crystals obtained above are as low as 26.23% which is not economical on a commercial scale.

ADVANTAGES

The previously described versions of the subject matter and its equivalent thereof have many advantages, including those which are described below.

The advantage of the present invention is that the ensilaging is carried out under controlled anaerobic conditions to fix and enrich the carotenoids and prevent the formation of unwanted oxidation products such as epoxides. Another advantage of the present invention is that 99% carotenoid esters in the enriched oleoresin can be saponified in less than 30 minutes. Further, the product obtained is not subjected to heat for a longer time to avoid the formation of degenerated oxidative products. The saponified mass is immediately precipitated with the aid of alcohol-water mixture under hot conditions aiding the removal of most of the impurities in a single step. The crystallized mass is filtered and washed with hot water to remove impurities. The wet crystals collected are dried to obtain carotenoids crystals. The complete process for obtaining the carotenoids crystals derived from marigold flower and/or flower petals is completed within 4-5 hours.

The present invention also has advantage in its organic friendly nature, time-temperature combination, and usage of safe class 3 solvents only. All these factors contribute towards the yield and stability of the product and bring down the cost of production on a commercial scale. It also increases the safety of the product for use as a nutraceutical, cosmeceutical, food or dietary supplement.

Another advantage is that the carotenoids crystals having different ratios of lutein and zeaxanthin crystals prepared by the process of the present invention result in a composition which is more bioactive and bioavailable.

Another advantage of the present invention is that it avoids the preparation of purified zeaxanthin crystals that have very low recoveries that is not economically viable.

We claim:
1. A process for isolation of carotenoids crystals having lutein and zeaxanthin in a weight ratio of about 10:1, 5:1 and 1:1 respectively, said process comprising:
   (a) contacting a plant source rich in lutein with an alcohol and extracting at a temperature of 50° C. to 75° C. to obtain an extract rich in lutein;
   (b) enriching the extract rich in lutein with an alcohol at a temperature in the range of 25° C. to 50° C. for 10 to 20 minutes to obtain an oleoresin rich in lutein;
   (c) contacting a plant source rich in zeaxanthin with an alcohol and extracting at a temperature of 50° C. to 75° C. to obtain an extract rich in zeaxanthin;
   (d) enriching the extract rich in zeaxanthin with an alcohol at a temperature in the range of 25° C. to 50° C. for 10 to 20 minutes to obtain an oleoresin rich in zeaxanthin;
   (e) mixing the oleoresin rich in lutein and the oleoresin rich in zeaxanthin in a ratio ranging from about 80:20 (w/w) to 90:10 (w/w), about 70:30 (w/w) to 30:70 (w/w) and about 10:90 (w/w) to 20:80 (w/w) respectively and homogenizing the mixture to obtain a mixed oleoresin;

(f) hydrolyzing the mixed oleoresin with an alcoholic alkali at a temperature in the range of 70° C. to 80° C. to obtain a reaction mixture; and (g) adding hot water at a temperature in the range of 70° C. to 75° C. to the reaction mixture to form a precipitate of carotenoids, thereby obtaining carotenoids crystals having lutein and zeaxanthin in a weight ratio of about 10:1, 5:1 and 1:1 respectively;

wherein the plant source rich in lutein and the plant source rich in zeaxanthin are independently selected from the group consisting of Marigold, Paprika and Chinese wolfberries (*Lycium barbarum*), the alcohol is selected from the group consisting of ethanol, isopropyl alcohol and mixtures thereof, and the alcoholic alkali is selected from the group consisting of ethanolic sodium hydroxide and ethanolic potassium hydroxide.

2. The process as claimed in claim 1, wherein the ratio of oleoresin to alcohol used for enriching the respective oleoresins is in the range of about 1:0.5 to 1:4 (w/v).

3. The process as claimed in claim 1, wherein the weight ratio of the reaction mixture to the hot water in step (g) is in the range of 1:1 to 1:1.4 (v/v).

4. The process as claimed in claim 1, wherein said oleoresin extracted from the plant source rich in lutein has a xanthophyll content in the range of 39 g/kg to 60 g/kg (3.9% to 6%) and wherein the oleoresin after being enriched has a xanthophyll content in the range of 115 g/kg to 145 g/kg (11.5% to 14.5%).

5. The process as claimed in claim 1, wherein said oleoresin extracted from the plant source rich in zeaxanthin has a xanthophyll content in the range of 6 g/kg to 21 g/kg (0.6% to 2.1%) and wherein the oleoresin after being enriched has a xanthophyll content in the range of 40 g/kg to 47 g/kg (4.0% to 4.7%).

6. The process as claimed in claim 1, further comprising:
(h) washing the carotenoids crystals with hot water at a temperature in the range of 55° C. to 80° C.; and drying the carotenoids crystals after being washed.

* * * * *